(12) United States Patent
Tang

(10) Patent No.: US 7,751,984 B2
(45) Date of Patent: Jul. 6, 2010

(54) IMAGE-BASED COMPUTATIONAL MECHANICAL ANALYSIS AND INDEXING FOR CARDIOVASCULAR DISEASES

(75) Inventor: Dalin Tang, Shrewsbury, MA (US)

(73) Assignee: Worcester Polytechnic Institute, Worcester, MA (US)

( * ) Notice: Subject to any disclaimer, the term of this patent is extended or adjusted under 35 U.S.C. 154(b) by 1244 days.

(21) Appl. No.: 11/296,943

(22) Filed: Dec. 8, 2005

(65) Prior Publication Data
US 2006/0149522 A1    Jul. 6, 2006

Related U.S. Application Data

(60) Provisional application No. 60/635,021, filed on Dec. 10, 2004.

(51) Int. Cl.
G06F 19/00 (2006.01)
G06K 9/00 (2006.01)

(52) U.S. Cl. .................. 702/19; D24/167; D24/181; 382/128; 382/130; 382/154

(58) Field of Classification Search .................. None
See application file for complete search history.

(56) References Cited

OTHER PUBLICATIONS

Osman et al. (IEEE Transactions on Medical Imaging (2000), vol. 19. pp. 186-202).*
Rekhter et al. (Circulation Research (2000) vol. 86, pp. 101-108).*
Tang, et al., "Effects of a Lipid Pool on Stress/Strain Distribution in Stenotiz Arteries: 3-D Fluid-Structure Interactions (FSI) Models", *J. Biomechanical Engineering*, 126, pp. 363-370 (2004).
Tang, D., et al., "3D Image-Based Computational Modeling for Patient-Specific Mechanical Analysis of Human Heart Right Ventricles," Paper presented at the meeting of the International Conference on Mathematics and Engineering Techniques in Medicine and Biological Sciences (METMBS), Las Vegas, NV (Jun. 2005).
Tang, D., et al., "Quantifying Effects of Plaque Structure and Material Properties on Stress Distributions in Human Atherosclerotic Plaques Using 3D FSI Models," *J. Biomechanical Engineering*, 127:1-10 (2005).
Tang, D., et al., "Local Maximal Stress Hypothesis and Computational Plaque Vulnerability Index for Atherosclerotic Plaque Assessment," *Annals of Biomedical Engineering*, 33(12): 1-13 (2005).
Tang, D., et al., "3D MRI-Based Multicomponent FSI Models for Atherosclerotic Plaques," *Annals of Biomedical Engineering*, 32(7): 947-960 (2004).
Bathe K. J., 1996, *Finite Element Procedures*. Prentice Hall, (Table of Contents Only).
Agresti, Alan, *Categorical Data Analysis*, 2nd Edition, Wiley & Sons, New York, 2002, (Table of Contents Only).
Schroeder, et al., 1998, *The Visualization Toolkit*, An Object-Oriented Approach to 3D Graphics, 2nd Edition, Prentice Hall, (Table of Contents Only).
Tang, et al. "Sensitivity analysis of 3D MRI-based models with fluid-structure interactions for human atherosclerotic coronary and carotid plaques," Editor: K. J. Bathe, *Computational Solid and Fluid Mechanics*, pp. 1009-1013, Elsevier, New York, 2005.
Kuehne T., et al, *Magnetic resonance imaging analysis of right ventricular pressure-volume loops*, Circ 110:2010-16 (2004).
Gerbeau, Jean-Frederic, et al., "Fluid-Structure Interaction in Blood Flows on Geometries coming from Medical Imaging," *Rapports de Recherche No. 5052*, Dec. 2003 (retrieved from the Internet: URL: http://www.ann.jussieu.fr/{frey/publications/RR-5052.pdf Retrieved Jul. 10, 2006).
Lee, K.W. et al., "Ultrasound image-based computer model of a common carotid artery with a plague," *Medical Engineering & Physics 26*(823-840), 2004.

* cited by examiner

*Primary Examiner*—Lori A Clow
(74) *Attorney, Agent, or Firm*—Hamilton, Brook, Smith & Reynolds, P.C.

(57) ABSTRACT

A method and a computer system, for providing an assessment for disease status of a disease, such as a cardiovascular disease, employ construction of image-based 3D computational model of an organ representative of the disease status; computationally obtaining a certain mechanical distribution using the 3D-organ model; and computational, quantitative analysis of the mechanical distribution to provide an assessment for disease status of a disease. The image-based 3D computational model includes a fluid-structure interaction and multiple components within the organ.

23 Claims, 18 Drawing Sheets

(a) In Vitro Stenosis Model Geometry (b) Stress vs. Severity (a) Stress-$P_1$, Thicker Cap (b) Stress-$P_1$, Thinner Cap Thick cap thickness = 0.8 mm; Thin cap thickness = 0.02mm;
Axial stretch: 10%, Stenosis severity (by diameter)=70%

(c) Maximal Stress Tracked at the Plaque Cap a) Very Stable  V=0 b) Stable Plaque V=1 c) Slightly Unstable  V=2 d) Vulnerable Plaque V=4

(a) MR Image  (b) Contour Plot (c) FE Mesh  (d) Histological Data (e) Reconstructed 3D Geometry of a 3D Coronary Plaque, 36 Slices (a) Global Maximal Stress Appears at Healthy Side (b) Local Maximal Stress Appeared at a Critical Site (c) Re-constructed Geometry of the Plaque Used in (a)

(a) Large Curvature Case (b) Thin Vessel Case

IMAGE-BASED COMPUTATIONAL MECHANICAL ANALYSIS AND INDEXING FOR CARDIOVASCULAR DISEASES

RELATED APPLICATION

This application claims the benefit of U.S. Provisional Application No. 60/635,021 filed on Dec. 10, 2004. The entire teachings of this provisional application are incorporated herein by reference.

GOVERNMENT SUPPORT

The invention was supported, in whole or in part, by a grant DMS-0072873 from the National Science Foundation and a grant NIH/NIBIB, 1 R01 EB004759-01 from the National Institute of Health. The Government has certain rights in the invention.

BACKGROUND OF THE INVENTION

Cardiovascular disease (CVD) is the No. 1 killer in the United States and responsible for 40% of all deaths in 2000. More than 60% of all myocardial infarction is caused by rupture of a vulnerable plaque. A large number of victims of the disease who are apparently healthy die suddenly without prior symptoms. About 95 percent of sudden cardiac arrest victims die before reaching a hospital. About 250,000 people a year die of coronary artery disease (CAD) without being hospitalized.

However, the mechanisms causing plaque rupture responsible for a stroke or cardiac arrest are poorly understood, and available screening and diagnostic methods are insufficient to identify the victims before the event occurs. For example, current technology for diagnosis of applicable cardiovascular diseases (e.g., carotid plaque rupture, coronary plaque rupture and aneurism rupture) generally lacks accurate and reliable computational mechanical analysis. Available MRI, CT, and ultrasound medical image equipment do not have computational mechanical analysis and related predictive computational indices for physicians to use in their decision making process. Even if some of the equipment may have some measurement data derived from some computational models, those models are overly simplified. The state of the art clinical decision making process is still based on morphologies derived from medical images with experiences from medical practice. Some 2D MRI-based models and 3D structure-only or fluid-only models have been known in the art. However, they are not generally adequate for decision-making purposes.

Therefore, a need exists for developing models adequate for decision-making purposes.

SUMMARY OF THE INVENTION

The present invention is generally directed to a method and to a computer system, for providing assessment for disease status of a disease using a three-dimensional multi-components model with fluid-structure interaction(s). The invention can provide a mechanical analysis of a disease, such as atherosclerotic plaques, aneurism, heart disease or heart (heart muscle) function.

In one embodiment, a method of the invention provides an assessment for disease status of a disease. The method comprises the steps of: a) constructing a computational, three-dimensional model of an organ (or biological system) representative of disease status of a disease based on data of the organ; b) computationally, obtaining a certain mechanical distribution using the three-dimensional organ model; and c) computationally applying quantitative analysis of the mechanical distribution to provide an assessment for disease status of a disease. The organ data includes image data of the organ, and the three-dimensional model includes a fluid-structure interaction and multiple components of the organ.

In another embodiment, the invention provides a computer system comprising: a) a data source containing data of an organ (or biological system) representative of disease status of a disease, the organ data including image data of the organ; b) a modeler generating a computational, three-dimensional model of the organ based on the organ data, said model including a fluid-structure interaction and multiple components of the organ, and c) a routine for computationally obtaining a certain mechanical distribution in the three-dimensional organ model, and for applying computational, quantitative analysis of the mechanical distribution. The quantitative analysis of the mechanical distribution provides assessment for said disease status of a disease.

Image-based clinical diagnosis in the art generally lacks mechanical analysis. Current technology for diagnosis of, for example, cardiovascular diseases (e.g., carotid plaque rupture, coronary plaque rupture and aneurism rupture), does not include an accurate and reliable computational mechanical analysis. Most decisions are made based on morphologies derived from medical images. Some 2D MRI-based models and 3D Structure-only or fluid-only models known in the art are not generally adequate for decision-making purposes. In those models, mechanical analysis is either ignored or performed based on deficient models.

Advantageously, Applicant's invention employs a three-dimensional model of an organ or biological system that includes fluid-structure interactions (e.g., blood-vessel interactions) and the structure of the organ or biological system. The three-dimensional models of the invention further include various components of the organ or biological system, e.g., various plaque components for atherosclerotic plaques. Therefore, the invention can accurately model mechanical distribution(s), such as stress/strain distribution(s), in the organ or biological system under investigation. Also, Applicant's invention can identify mechanical biological index (indices) to quantify the degree of the disease status, which can help physicians in decision-making processes.

The methods and computer systems of the invention are applicable to various diseases, such as cardiovascular diseases. For example, the present invention can be used for diagnosing carotid plaque rupture and coronary plaque rupture or aneurism rupture. Also, the present invention can be used in computer-guided heart surgery.

BRIEF DESCRIPTION OF FIGURES

The foregoing and other objects, features and advantages of the invention will be apparent from the following more particular description of preferred embodiments of the invention, as illustrated in the accompanying drawings. The drawings are not necessarily to scale, emphasis instead being placed upon illustrating the principles of the invention.

DETAILED DESCRIPTION OF THE INVENTION

Figure 1:
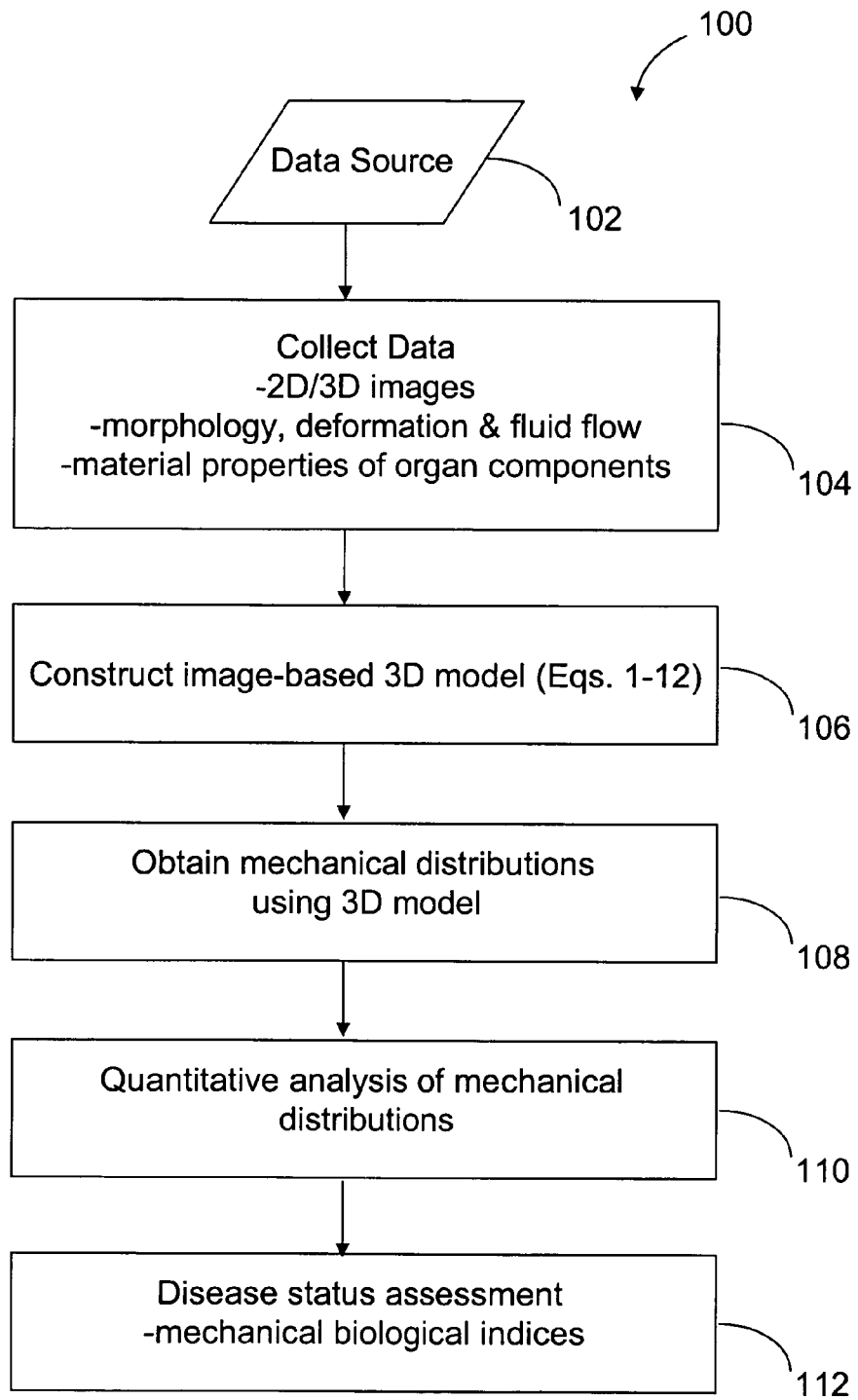
FIG. 1 is a flow diagram of one embodiment of the present invention.

Generally, the present invention employs construction 106 of an image-based, three-dimensional (3D) computational model of an organ representative of interest (e.g., an organ representative of disease status of a certain disease); computationally obtaining 108 certain mechanical distribution(s) using the 3D-organ model; and quantitative analysis 110 of the mechanical distribution(s), providing assessment for the disease status (see FIG. 1). Preferably, the quantitative analysis leads to identification of mechanical biological index (indices) 112 which can be used to quantify the degree of a disease state. FIG. 1 is illustrative and represents one embodiment of the present invention.

For the construction of the 3D organ model (step 106), the invention typically includes collecting data (step 104) of an organ that is representative of disease status of a disease under investigation. As used herein, the term "organ" means a biological system, such as the heart, hear muscles and artery. The data is from data source 102 and includes image data of the organ, for example, 2D and/or 3D image data (in vivo, ex vivo and/or in vitro data). Preferably, the image data includes in vivo and/or ex vivo image data (2D and/or 3D data, preferably 3D data). Examples of image data include magnetic resonance imaging (MRI) and ultrasound/doppler measurements data. More preferably, the image data includes image data of components of the organ under investigation, such as 2D or 3D MRI data of plague components (e.g., calcification, lipid rich necrotic core and fibrous tissue).

In one embodiment, the data for an organ (e.g., artery having plaque(s) or the heart muscles) that is representative of disease status of a disease include data from three aspects: morphology (e.g., morphology of plaques), deformation (e.g., organ structural deformation), and fluid flow information (e.g., blood pressure, blood flow velocity profile and temporal pressure profile) data of the organ. In a preferred embodiment, the data further includes material data, such as material properties of components of the organ (e.g., material properties of calcification, lipid rich necrotic core and fibrous tissue of plaques). In a specifically preferred embodiment, the data includes patient-specific data, such as patient-specific, fluid flow, morphology and/or deformation data. In another specifically preferred embodiment, the data includes patient-specific material data. In an even more preferred embodiment, the data includes in vivo and/or ex vivo 3D image data of the organ, and patient-specific fluid flow, morphology, deformation, and/or material data. In this embodiment, preferably, the 3D image data of the organ includes patient-specific 3D image data, preferably patient-specific 3D MRI data.

For 3D-reconstruction of organ geometry of the invention, a series of 2D and/or 3D images are used to reconstruct 3D geometry of the organ, e.g., plaques or heart muscles. For example, 3D MRI data sets of the organ are read by a software package, such as Atherosclerotic Plaque Imaging Analysis (APIA, MathWorks, MATLAB, Natick, Mass.) or the Visualization Toolkit (VTK, see Schroeder, et al. *An Object-Oriented Approach to 3D Graphics*, 2nd Ed. Prentice Hall (1998), the entire teachings of which are incorporated herein by reference), and 3D geometry of the organ and computational mesh are reconstructed.

In one embodiment, 3D MRI data sets consisting of 2D slices are used for constructing 3D models of artery having plaque(s), such as carotid plaques. In this example, boundary lines for various plaque components (lipid-rich necrotic pools, calcification, hemorrhage, vessel, etc.) are generated according to data ranges validated by histological data for each slice. When ex vivo plaque sample data is used, a vessel layer of, for example, 0.5-1.0 mm thickness, is added to models of the plaque samples to account for the artery part. When in vivo plaque sample data is used, addition of a vessel layer to the models is not necessary, because the in vivo plaque sample data includes the artery part (see, for example, Tang, et al, *Annals of Biomedical Engineering*, 32(7), pp. 947-960 (2004), the entire teachings of which are incorporated herein by reference).

The computational 3D model of an organ constructed as described above includes fluid-structure interaction(s) (FSI), such as blood-vessel interaction(s). Preferably, the computational 3D model includes FSI, solid-to-solid interaction(s) and components of the organ. More preferably, patient-specific data, such as patient-specific, fluid flow, morphology, deformation, and/or material data, are employed for construction of the 3D model.

In one example, computational 3D models for an artery having plaque(s) or the heart (e.g., the right or left ventricle) can be constructed using equations (1)-(12) below. For a solid model, solid materials of the model, such as artery vessel material, heart muscles and solid components of the organ (e.g. plaque components), are typically assumed to be hyperelastic, isotropic or anisotropic, incompressible and homogeneous. For a fluid model, the flow is assumed to be laminar, Newtonian, viscous and incompressible. The incompressible Navier-Stokes equations with arbitrary Lagrangian-Eulerian (ALE) formulation are used as the governing equations which are suitable for FSI problems with frequent mesh adjustments. A 3D nonlinear, modified Mooney-Rivlin (M-R) model is used to describe the material properties of the vessel wall, muscle (e.g., heart muscle) and organ components (e.g., plaque components). No-slip conditions and natural traction equilibrium conditions are assumed at all interfaces. Putting these together, the following equations are obtained (summation convention is used):

$$\rho(\partial u/\partial t+((u-u_g)\cdot\nabla)u)=-\nabla p+\mu\nabla^2 u, \quad (1)$$

$$\nabla\cdot u=0, \quad (2)$$

$$u|_\Gamma=\partial x/\partial t,\ \partial u/\partial n|_{inlet,outlet}=0, \quad (3)$$

$$p|_{inlet}=p_{in}(t),\ p|_{outlet}=p_{out}(t), \quad (4)$$

$$\rho v_{i,tt}=\sigma_{ij,j},\ i,j=1,2,3;\ \text{sum over j}, \quad (5)$$

$$\epsilon_{ij}=(v_{i,j}+v_{j,i})/2,\ i,j=1,2,3 \quad (6)$$

$$\sigma_{ij}\cdot n_j|_{out\_wall}=0, \quad (7)$$

$$\sigma^f_{ij}\cdot n_j|_{interface}=\sigma^s_{ij}\cdot n_j|_{interface}, \quad (8)$$

where u and p are fluid velocity and pressure, $u_g$ is mesh velocity, $\Gamma$ stands for vessel inner boundary, $f\cdot,_j$ stands for derivative of f (f stands for a general function, such as v or $\sigma$) with respect to the jth variable, $\sigma$ is stress tensor (superscripts indicate different materials), $\epsilon$ is strain tensor, v is solid displacement vector. The strain energy function for the modified Mooney-Rivlin (M-R) model is given by, $$W=c_1(I_1-3)+c_2(I_2-3)+D_1[\exp(D_2(I_1-3))-1], \quad (9)$$

where $I_1$ and $I_2$ are the first and second strain invariants, $c_i$ and $D_i$ are material constants chosen to match experimental measurements and data available in the literatures. The stress/strain relations can be found by:

$$\sigma_{ij}=(\partial W/\partial\epsilon_{ij}+\partial W/\partial\epsilon_{ji})/2, \quad (10)$$

where $\sigma_{ij}$ are the second Piola-Kirchhoff stresses, $\epsilon_{ji}$ are the Green-Lagrange strains. The incremental material law is evaluated by further differentiation as:

$$C_{ijrs}=(\partial\sigma_{ij}/\partial\epsilon_{rs}+\partial\sigma_{ij}/\partial\epsilon_{sr})/2 \quad (11).$$

The incremental generalized Hooke's law is given by:

$$\sigma_{ij}=C_{ijrs}\epsilon_{rs} \quad (12).$$

Various specific values for the parameters in the equations above can be used depending upon various case studies. Further details about the models can be found in Tang, et al., *Annals of Biomedical Engineering*, 32(7), pp. 947-960 (2004) and Tang, et al., *J. Biomechanical Engineering*, 126, pp. 363-370 (2004), the entire teachings of which are incorporated herein by reference.

The fully-coupled fluid and structure models can be solved by computer software, such as a commercial finite-element package ADINA® (ADINA® R&D, Inc., Watertown, Mass., USA). ADINA® uses unstructured finite element methods for both fluid and solid models. Nonlinear incremental iterative procedures can be used to handle fluid-structure interactions. The governing finite element equations for both the solid and fluid models can be solved by, for example, Newton-Raphson iteration method. Proper computer mesh is chosen to fit the shape of each component, vessel, muscle, and the fluid domain that are included in the 3D model of the organ. For example, for a 3D model of plaques, finer mesh can be used for thin plaque cap and components with sharp angles to get better resolution and handle high stress concentration behaviors. The artery models can be stretched axially and pressurized gradually to specified conditions. Unsteady simulation, for example, under pulsating pressure conditions, can then be followed. Typically, mesh analysis is performed until differences between solutions from two consecutive meshes are negligible (e.g., less than about 1% in $L_2$ norm). Exemplary computational models and solution methods can be found in Tang et al.

In a preferred embodiment, constructing the FSI models of the invention further includes updating the computing domain for both fluid and structure models, and adjusting the corresponding computational meshes. In another preferred embodiment, construction of the FSI models of the invention includes cutting the structure geometry into many small volumes until a convergent model is reached.

At step 108, computationally obtaining certain mechanical distribution(s), such as stress/strain distribution(s), can be done by the use of 3D FSI models of the invention, as described above. As used herein, the term "stress/strain distribution" means the values of stress and strain tensors on the entire computational domain. In one embodiment, the mechanical distribution includes structural stress/strain distribution(s). In another embodiment, the mechanical distribution includes fluid flow (e.g., blood flow) and structure stress/strain distribution(s). Preferably, the mechanical distribution includes fluid velocity, pressure, shear stress and structure stress/strain distributions.

Next, quantitative analysis (step 110) of the mechanical distribution(s) using the computational 3D FSI models provides assessment for disease status of a disease. Preferably, the assessment for disease status of a disease is in a digital format. More preferably, the assessment for disease status in a digital format leads to identification of mechanical biological index (indices) 112 which are used to quantify the degree of a disease.

In one embodiment, the quantitative analysis 110 provides assessment (e.g. computational mechanical indices 112) for plaque vulnerability to rupture. The quantitative analysis for the plaque vulnerability to rupture includes identifying one or more critical sites where plaque(s) is vulnerable to rupture. As used herein, the term "critical site" means a location which may be related to plaque rupture. Certain mechanical distribution(s), such as stress/strain distribution(s), on the identified critical sites is analyzed using 3D FSI model(s) of an artery including plaque(s), as described above. The quantitative analysis 110 further includes scaling the plaque(s) at the critical sites in a numeric format by comparing the plaque(s) at the critical sites and the mechanical distribution(s) on the critical sites with a standard value. The standard value for plaques vulnerability to rupture in one embodiment is provided by analyzing pathological data of plaques, and classifying vulnerability of the plaques used for the pathological analysis in a numeric format (histopathological vulnerability indices (HPVI)), or by analyzing long-term tracking data of patients with advanced plaques and rate of clinical events (actual rupture rate). Correlating (e.g., regressively correlating) the numerical values of the plaque(s) at the critical sites with the standard value provides numerical assessment for plaque rupture. Preferably, the step 110 of analyzing mechanical distribution(s) includes quantifying at least one of: effect of pulsating pressure condition; effect of morphology (e.g., plaque cap thickness); and effect of material properties of multiple components of the organ, on stress and strain behaviors of blood flow and plaque. More preferably, the pulsating pressure condition; morphology (e.g., plaque cap thickness); and material properties of multiple components of the organ are patient-specific.

Generally, plaque rupture involves many controlling factors. For example, mechanical forces, structural features and material properties can affect mechanical forces in plaques, which determine the vulnerability of the plaques to rupture. Examples of such mechanical forces include blood pressure, shear stress, stretch, residual stress, tethering and motion. Examples of structural features include plaque morphology, vessel geometry, vessel thickness, lumen, plaque components, lipid shape and size, cap thickness, calcification, hemorrhage and surface weakening. Examples of material properties include material parameters for vessel and plague components, such as fibrous cap, lipid and calcification, luminal surface weakening or erosion. The computational 3D models of the invention capture the major controlling factors affecting mechanical forces in the plaque(s). Preferably, patient-specific data, for example, blood pressure, vessel geometry, plague morphology, plaque components and the like, are employed in the invention.

Figure 2:
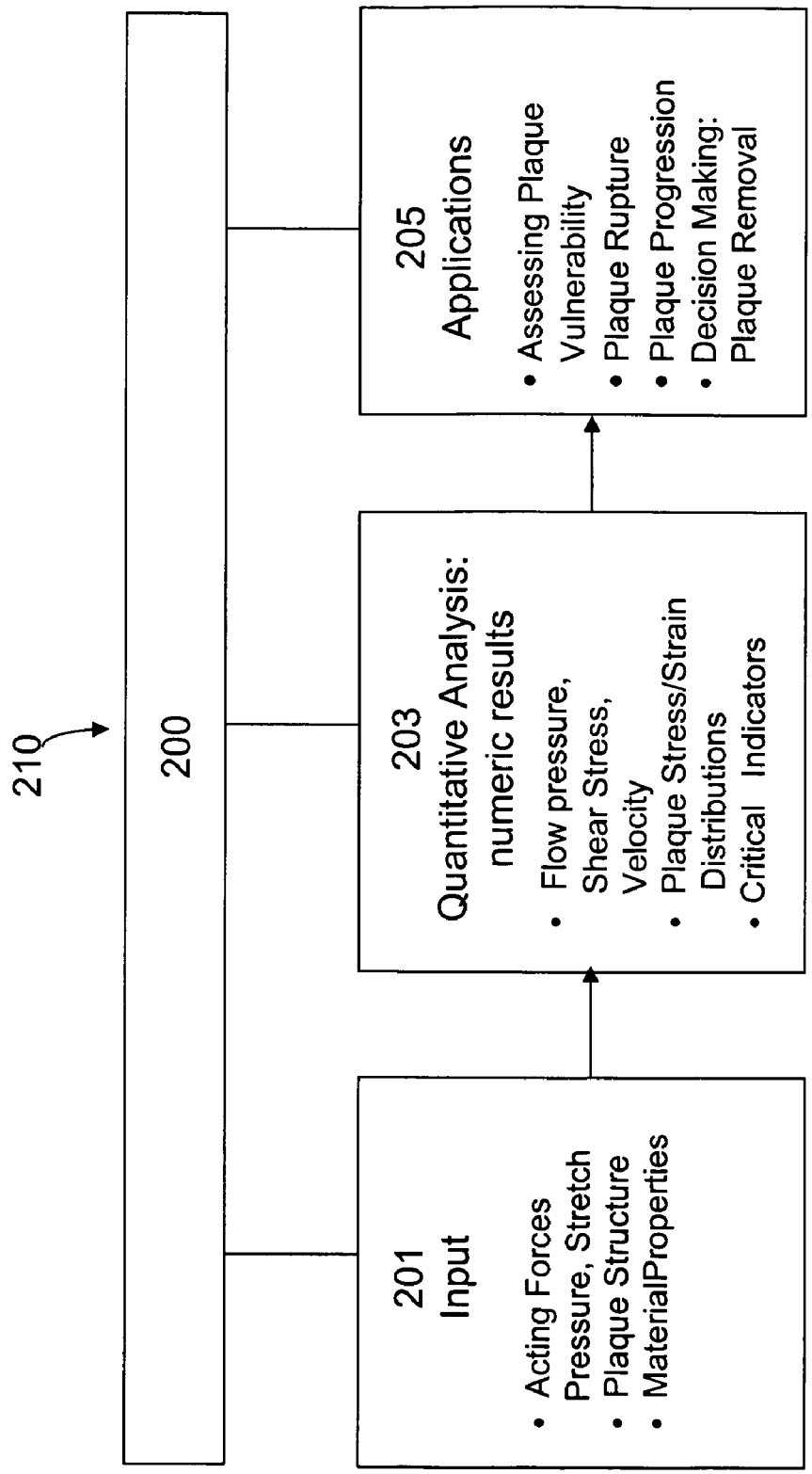
FIG. 2 is a schematic illustration of one embodiment of the present invention, providing assessment for plaque vulnerability to rupture.

FIG. 2 shows one embodiment 210 of the invention for providing assessment for plaque vulnerability to rupture, including a three-step modeling process. In the illustrated example, input data 201 such as pressure, stretch, acting forces, plaque structure and material properties are used for constructing 3D FSI model(s) 200 of one or more arteries having plaque(s). The 3D FSI model(s) 200 constructed from those input data 201 are then used for computationally obtaining plaque stress/strain distributions, and/or flow pressure, shear stress and velocity. A numerical method 203 is used to obtain initial stress/strain fields in the plaque, and model material parameters for the artery (vessel) and plaque components. Quantitative analysis (203) of the plaque stress/strain distributions, and/or flow pressure, shear stress and velocity provide the critical indicators (e.g. numerical indicators) which are used for assessing plaque vulnerability. Physicians can then use the critical indicators in diagnosing and/or decision-making process 205 for the plaque(s) under investigation (e.g., plaque progression, plaque rupture, or plaque removal).

In one specific embodiment, for providing assessment for plaque vulnerability to rupture, a method (at 203) of the invention provides the assessment preferably by identifying and analyzing a local maximum stress/strain in arteries having plaques, rather than by an overall maximum stress/strain. Herein, the "local maximal stress/strain value" is the greatest value in a surrounding neighborhood. In a specific example, a "critical site tracking (CST)" or "critical site selection (CSS)" approach is used to concentrate on plaque stress/strain behavior(s) at well-selected critical sites. Examples of critical sites include locations of local maxima, locations of very thin cap and any sites of special interest. In a preferred embodiment, stress/strain distributions as well as their variations are computationally simulated under pulsating pressure conditions using the 3D FSI models 200 of the invention. In another embodiment, plaque samples with large calcifications and large lipid pools are used to demonstrate effects of plaque components on stress/strain distributions. Cap thickness and material strength can be varied to quantify corresponding stress/strain changes.

Preferably, search for the local maxima and their sites are programmed to be performed automatically. Stress/strain values at the local maxima are grouped by site category, analyzed by standard statistical methods known in the art, and the group showing correlation with HPVI are chosen as the "critical site" (CS) stress/strain values.

The present invention, optionally, further employs validation of the numerical assessment for a disease status of a disease, such as plaque rupture vulnerability, when relevant clinical data becomes available. In one embodiment, histopathological analysis is used as a "gold standard" for validations of computational findings. In one specific embodiment, a semi-quantitative histopathological method is used to obtain the gold standard. The method includes classifying an organ representative of disease status (e.g., plaques) into different grades according to factors known to correlate with the disease status (e.g., morphology, vessel geometry, vessel thickness, lumen, plaque components, lipid shape and size, cap thickness, calcification, hemorrhage and surface weakening for assessing plaque vulnerability). This histopathological classification is then used as the gold standard to validate the computational index (indices) 112 of the invention.

When assessment for plaque vulnerability is provided, patient-tracking data analysis preferably includes data obtained from long-term tracking patients (especially data obtained close to the fatal event) together with the actual occurring rate of heart attack and stroke serve as the "gold standard" for the validation. The long-term tracking patients are generally those who have had a stroke or heart attack, and major changes already have happened in the plaques when the plaques are removed for study. It may be very desirable to track those vulnerable patients at a much earlier time.

In a preferred embodiment, the method and computer system (processor routine) 100 of the invention provide assessment for disease status of a cardiovascular disease. In one specifically preferred embodiment, the organ or biological system under investigation is an artery having plaques. In this embodiment, preferably, the computational 3D modeling 106, 108 includes: unsteady stress/strain variations at critical locations under pulsating pressure conditions; sensitivity studies of stress/strain behaviors on plaque components (especially large calcifications and lipid-rich necrotic cores), plaque cap thickness, cap erosion, stenosis severity, and material properties of vessel and plaque components. More preferably, the computational 3D modeling 106, 108 can further include a computational plaque vulnerability index (CPVI) based on histopathological plaque classifications. In another preferred embodiment, the 3D model can further include factors: multi-layered vessel structure; anisotropic properties of the vessel; viscoelastic properties of the vessel; vessel inner surface condition, inflammation; residual stress; blood conditions, cholesterol, chemical environment; cell activities, plaque progression and remodeling; non-Newtonian flow properties; and/or turbulence.

In another preferred embodiment, the organ includes a heart muscle, such as the right ventricle of the heart. Preferably, the 3D FSI modeling of heart muscles includes a structure model for the heart, a fluid model for blood and a force field. The force field is introduced to the structure model as a force to govern heart muscle contraction and relaxation. The force field is a 3D tensor function provided to simulate heart muscle contraction. The force field is chosen so that the simulated heart contraction matches actual heart motion measured by medical image technology such as tagged MRI. Computational modeling of heart muscles of the invention can be used in computer-aided cardiac surgery.

Figure 3:
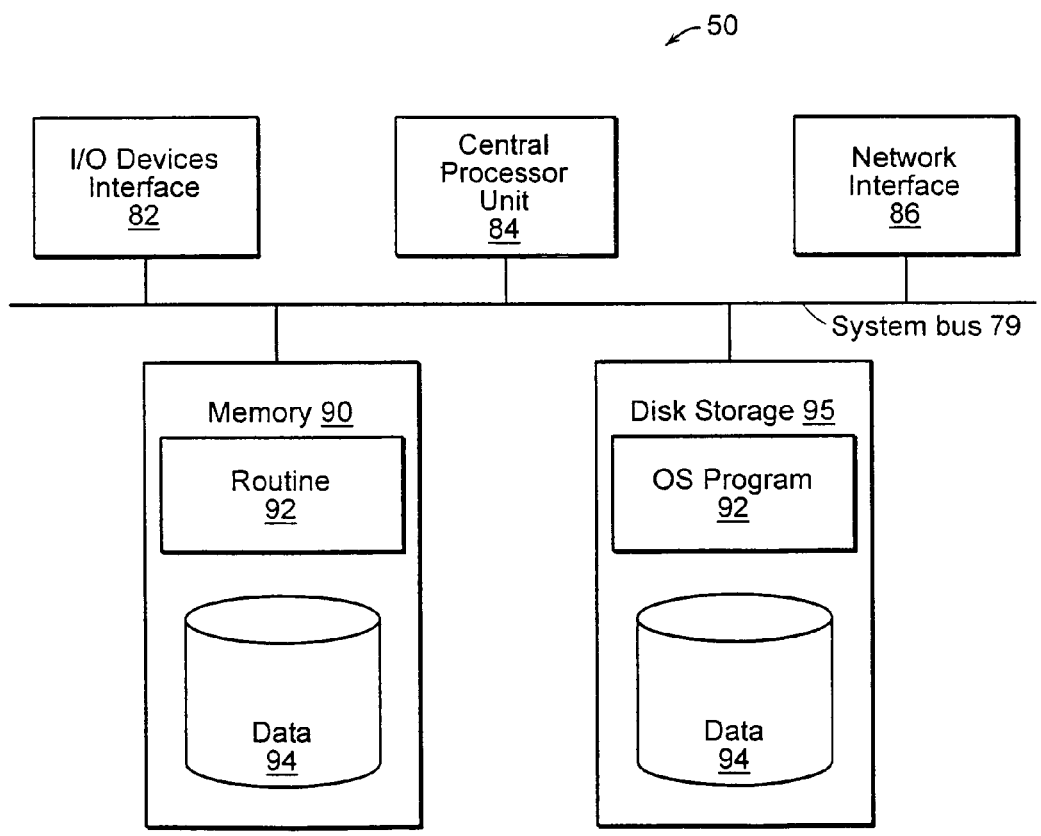
FIG. 3 is a block diagram of a computer system in which embodiments of the present invention are deployed.

FIG. 3 is a diagram of the internal structure of a computer 50. The computer 50 contains system bus 79, where a bus is a set of hardware lines used for data transfer among the components of a computer or processing system. Bus 79 is essentially a shared conduit that connects different elements of a computer system (e.g., processor, disk storage, memory, input/output ports, network ports, etc.) that enables the transfer of information between the elements. Attached to system bus 79 is I/O device interface 82 for connecting various input and output devices (e.g., keyboard, mouse, displays, printers, speakers, etc.) to the computer 50. Network interface 86 allows the computer to connect to various other devices attached to a network (e.g., a wide area network, a local area network or global computer network). Memory 90 provides volatile storage for computer software instructions 92 and data 94 used to implement an embodiment of the present invention (e.g., computational model and analysis systems and methods 100, 210 detailed above and in FIGS. 1 and 2). Disk storage 95 provides non-volatile storage for computer software instructions 92 and data 94 used to implement an embodiment of the present invention. Central processor unit 84 is also attached to system bus 79 and provides for the execution of computer instructions.

In one embodiment, the processor routines 92 and data 94 are a computer program product (generally referenced 92), including a computer readable medium (e.g., a removable storage medium such as one or more DVD-ROM's, CD-ROM's, diskettes, tapes, etc.) that provides at least a portion of the software instructions for the invention system. Computer program product 92 can be installed by any suitable software installation procedure, as is well known in the art. In another embodiment, at least a portion of the software instructions may also be downloaded over a cable, communication and/or wireless connection. In other embodiments, the invention programs are a computer program propagated signal product embodied on a propagated signal on a propagation medium (e.g., a radio wave, an infrared wave, a laser wave, a sound wave, or an electrical wave propagated over a global network such as the Internet, or other network(s)). Such carrier medium or signals provide at least a portion of the software instructions for the present invention routines/program 92.

In alternate embodiments, the propagated signal is an analog carrier wave or digital signal carried on the propagated medium. For example, the propagated signal may be a digitized signal propagated over a global network (e.g., the Internet), a telecommunications network, or other network. In one embodiment, the propagated signal is a signal that is transmitted over the propagation medium over a period of time, such as the instructions for a software application sent in packets over a network over a period of milliseconds, seconds, minutes, or longer. In another embodiment, the computer readable medium of computer program product 92 is a propagation medium that the computer system 50 may receive and read, such as by receiving the propagation medium and identifying a propagated signal embodied in the propagation medium, as described above for computer program propagated signal product.

Generally speaking, the term "carrier medium" or transient carrier encompasses the foregoing transient signals, propagated signals, propagated medium, storage medium and the like.

EXEMPLIFICATION

Example 1

Unsteady Stress Variations in Human Atherosclerotic Plaques and Sensitivity Analysis Using 3D MRI-Based Fluid-Structure Interactions (FSI) Models This example illustrates methods and computer systems 100, 210 of the invention for providing assessment for plaque vulnerability to rupture.

An unsteady three-dimensional (3D) MRI-based computational model for human atherosclerotic plaques with multi-component plaque structure and fluid-structure interactions (FSI) was introduced to perform mechanical analysis and identify critical flow and stress/strain conditions which might be related to plaque rupture.

Also, in this example, "local" maximal stress/strain values and their variations were investigated. A "critical site tracking" (CST) approach was used to concentrate on plaque stress/strain behaviors at well-selected critical locations which include locations of local maxima, locations of very thin cap and any sites of special interest. Stress/strain distributions as well as their variations under pulsating pressure conditions were investigated using 3D MRI-based multi-component FSI models. Plaque samples with large calcifications and large lipid pools were used to demonstrate effects of plaque components on stress/strain distributions. Cap thickness and material strength were varied to quantify corresponding stress/strain changes.

1A 3D MRI-Based Computational Model and Cases Studied 1A.1 The Solid and Fluid Models.

For the fluid model, the flow was assumed to be laminar, Newtonian, viscous and incompressible. The incompressible Navier-Stokes equations with arbitrary Lagrangian-Eulerian (ALE) formulation were used as the governing equations which were suitable for FSI problems with frequent mesh adjustments. Both artery vessel material and plaque components in the plaque were assumed to be hyperelastic, isotropic, incompressible and homogeneous. The 3D nonlinear modified Mooney-Rivlin (M-R) model was used to describe the material properties of the vessel wall and plaque components. No-slip conditions and natural traction equilibrium conditions were assumed at all interfaces. The 3D models were constructed using equations (1)-(13) with the following values chosen for the baseline models: vessel material: $c_1=92,000$ dyn·cm$^{-2}$, $c_2=0$, $D_1=36,000$ dyn·cm$^{-2}$, $D_2=2$; lipid-rich core: $c_1=5,000$ dyn·cm$^{-2}$, $c_2=0$, $D_1=5,000$ dyn·cm$^{-2}$, $D_2=1.5$; calcification: $c_1=920,000$ dyn·cm$^{-2}$, $c_2=0$, $D_1=360,000$ dyn·cm$^{-2}$, $D_2=2$. These parameter values were used in the various case studies of Example 1 unless changed explicitly for parameter evaluation purposes. Further details about the models can found from Tang, et al., *Annals of Biomedical Engineering*, 32(7), pp. 947-960 (2004) and Tang, et al., *J. Biomechanical Engineering*, 126, pp. 363-370).

1A.2 Cases Studied and Fixation Procedures

A 3D MRI data set obtained from a human coronary plaque ex vivo consisting of 36 slices with a relatively high resolution (0.25 mm×0.23 mm×0.5 mm) and a set obtained from a human carotid plaque ex vivo consisting of 64 2D slices with higher spatial resolution (0.1 mm×0.1 mm×0.5 mm) were used as the baseline cases to develop the computational model. To add clinical relevance to this mechanical analysis study, additional 18 coronary artery segments (2D) were selectively collected from 8 autopsy patients (6M, 2F, aged 60±15 years). Four patients died of coronary artery disease (CAD). All specimens were fixed in a 10% buffered formalin solution and placed in a polyethylene tube. They were stored at 4° C. within 12 hours after removal from the heart. MRI imaging was taken within 2 days at room temperature. After completion of MR study, the transverse sections with a thickness of 10 μm were obtained at 1 mm intervals from each specimen. These paraffin-embedded sections were stained with hematoxylin and eosin (H&E), Masson's trichrome, and elastin van Gieson's (EVG) stains to identify major plaque components: calcification (Ca), lipid rich necrotic core (LRNC), and fibrotic plaques (FP). Plaque vulnerability of these samples was assessed pathologically to serve as bench mark to validate computational findings.

To perform sensitivity analysis, in vitro stenosis models (see, for example, Tang, et al., *J. Biomechanical Engineering*, 126, pp. 363-370 (2004)) and samples with material properties and geometries modified from the real plaques were also used in the simulations so that effects of material properties (vessel, calcification, and lipid core), plaque cap thickness, and plaque stenosis severity can be quantified on comparable bases. Each parameter or controlling factor under investigation was varied incrementally within physiological range and 8-10 cases were considered while other parameters and modeling conditions were kept unchanged.

1A.3 3D Re-Construction of Plaque Geometry.

Figure 4:
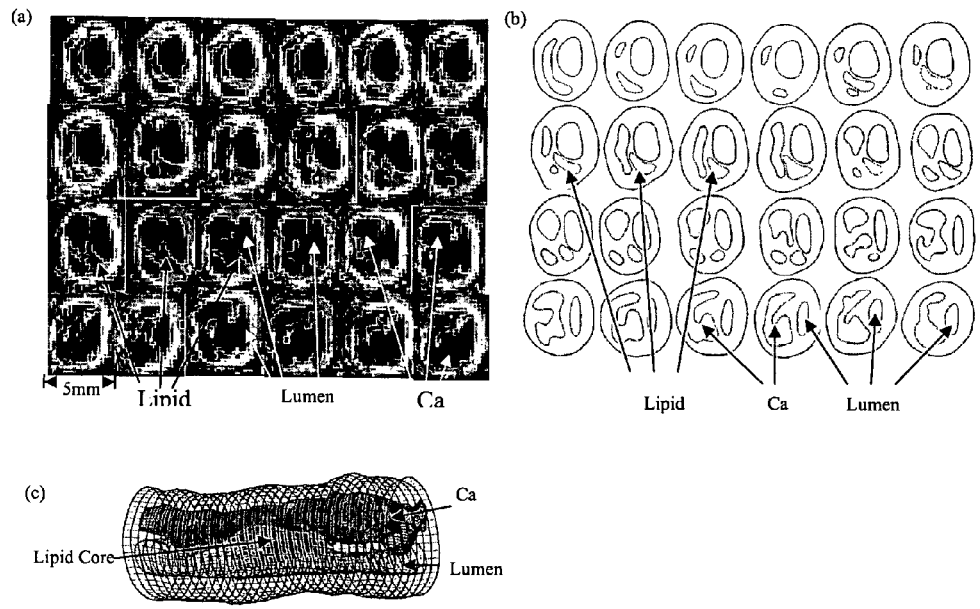
FIGS. 4(a)-4(c) show a cadaveric plaque sample with a large calcification block and a lipid pool for a three-dimensional (3D) model of the invention: (a) Selected MR images from a 36-slice set (S9-S32 from left to right, then continued to next row); (b) Component segmentations of MR images based on histological data; (c) Reconstructed 3D plaque geometry of the plaque sample of FIG. 4(a).

3D ex vivo MRI data sets obtained from human atherosclerotic plaques with high resolution were read by VTK (see, for example, Schroeder, et al., 1998, *The Visualization Toolkit*, An Object-Oriented Approach To 3D Graphics, 2nd Edition, Prentice Hall, the entire teachings of which are incorporated herein by reference) and 3D plaque geometry and mesh were re-constructed following the procedure described in Tang (see, for example, Tang, et al, *Annals of Biomedical Engineering*, 32(7), pp. 947-960 (2004)). Boundary lines for various plaque components were generated according to segmentation data ranges validated by histological analysis. FIGS. 4(a)-4(c) show 24 MRI slices (selected from a set of 36 slices) of a cadaveric human coronary plaque sample, plaque component contour plots based on histological segmentation data, and the re-constructed 3D geometry. The diameter of the vessel was about 5-6 mm. Some smoothing was applied. The vessel was extended uniformly at both ends by 3 cm and 6 cm respectively so that it became long enough for the simulations of this example. Geometries of other plaque samples were constructed using the same procedures.

1A.4 Solution Method

The fully coupled fluid and structure models were solved by a commercial finite-element package ADINA® (ADINA® R & D, Inc., Watertown, Mass., USA). Nonlinear incremental iterative procedures were used to handle fluid-structure interactions. The governing finite element equations for both the solid and fluid models were solved by Newton-Raphson iteration method. Proper mesh was chosen to fit the shape of each component, the vessel, and the fluid domain. Finer mesh was used for thin plaque cap and components with sharp angles to get better resolution and handle high stress concentration behaviours. The artery was stretched axially and pressurized gradually to specified conditions before the unsteady simulation under pulsating pressure conditions. Mesh analysis was performed until differences between solutions from two consecutive meshes were negligible (less than 1% in $L_2$-norm). Details of the computational models and solution methods can be found from Tang et al. references cited above.

1B.1 Baseline Results.

Stress/strain behaviors corresponding to pulsating pressure, plaque structure, and plaque material properties were investigated. A computational plaque grading scheme to quantify plaque vulnerability was applied to 18 2D plaque samples and results were compared with histopathological classifications.

A coronary plaque with a large calcification block and a lipid core was selected as the baseline example because it would demonstrate that large plaque structures had considerable effects on stress/strain behaviors (see FIGS. 4(a)-4(c)). The plaque had a large calcification which occupied about 30% volume of the plaque, a smaller lipid-rich necrotic core ("lipid core" hereinafter), offering reasonable complexity as desired. The plaque severity by area (reduction of lumen area compared to healthy portion of the vessel) was about 71%. Boundary conditions for the baseline model were set as follows: Pulsating upstream pressure $P_{in}$=90-150 mmHg, downstream pressure $P_{out}$=89.5-126 were chosen to represent a typical high pressure case (see FIGS. 5(a)-5(b)). Corresponding flow rate was between 2-15 ml·s$^{-1}$ and (see FIG. 5(b)). A 10% axial pre-stretch was applied.

Figure 6:
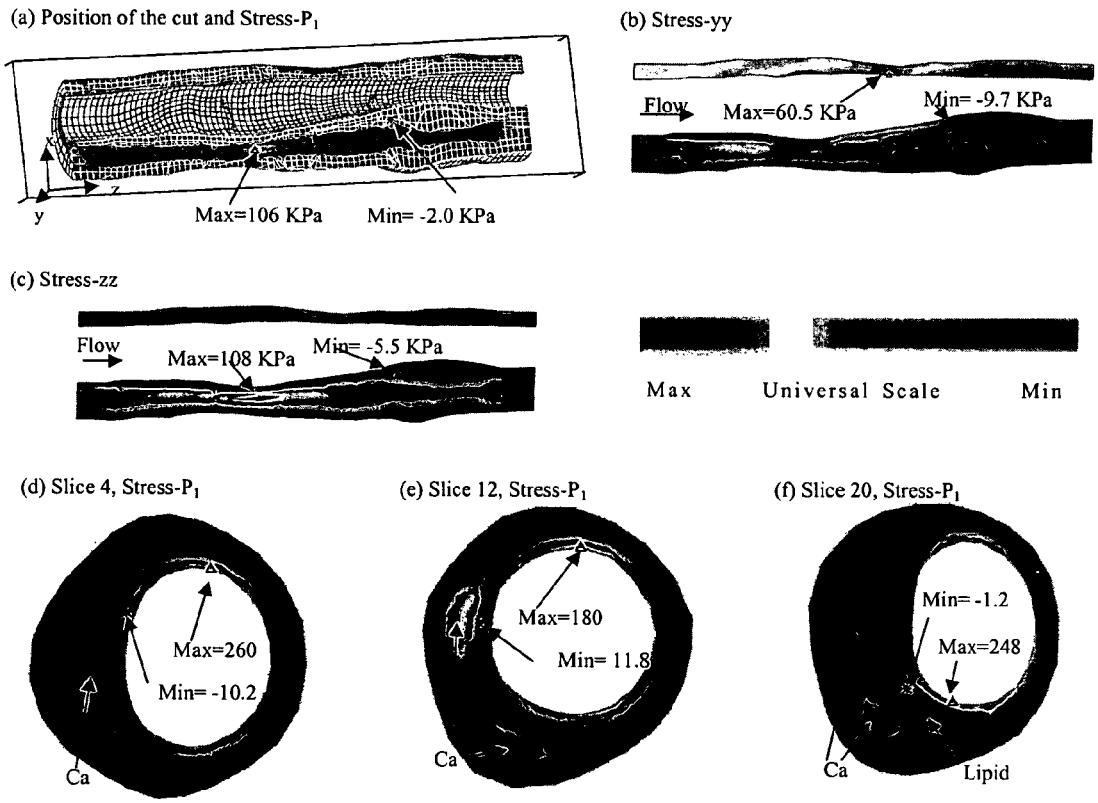
FIGS. 6(a)-6(f) show band plots of selected stress components from a 3D FSI baseline model of the invention on a sagittal slice and three cross-sectional cuts showing that a large calcification block has considerable effect on stress distributions ($P_{in}$=150 mmHg, $P_{out}$=126 mmHg, axial stretch=10%): (a) Position of the cut and band plot of Stress-P1 showing calcification has higher stress level; (b) Band plot of circumferential stress distribution showing a maximum value is found at a healthy side of the vessel where vessel wall is thin; (c) Band plot of longitudinal tensile stress; (d) Band plot of Stress-P1 on Slice 4 having one calcified region; (e) Band plot of Stress-P1 on Slice 12 having two calcifications; (f) Band plot of Stress-P1 on Slice 20 having two calcifications and one lipid core.

The entire 3D computational fluid and structure domains were searched (by examining numerically-cut serial sagittal and axial slices) for critical stress/strain values and patterns. Band plots of stress distributions of several components on one sagittal cut and several cross-sectional cuts at the time when $P_{in}$=150 mmHg and $P_{out}$=126 mmHg condition are given in FIGS. 6(a)-6(f). FIG. 6(a) shows the position of the cut, and also gives Stress-P1 (maximum principal stress) on the whole sagittal cut showing a maximum value located in the calcified region where its vessel wall is thin. FIG. 6(b) gives band plot of Stress-yy (circumferential tensile stress) showing a maximum value located at a healthy part of the vessel because of its thin vessel thickness. FIG. 6(c) shows band plot of Stress-zz, tensile stress in the axial direction. All the band plots show that minima of those stress components are found where the vessel wall is thick, i.e., stress level is lower where plaque is more severe.

FIGS. 6(d)-6(f) show band plots of Stress-P1 on three selected cross-section cuts: Slice 4 had only one calcified region; Slice 12 had two calcifications; Slice 20 had two calcifications and a lipid core. A maximum was observed at the thin cap of the lipid core from FIG. 6(f). It was also clear that the calcification had considerable effect on stress distributions, especially when it became the main support of the plaque structure.

1B.2 Unsteady Stress/Strain Behaviours at Critical Sites under Pulsating Pressure.

Figure 7:
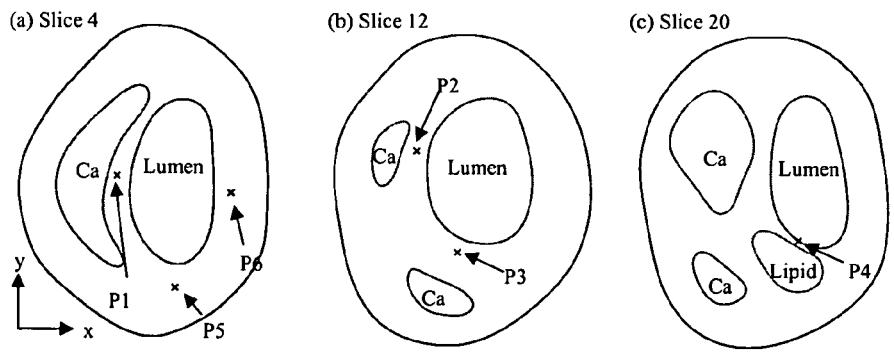
FIGS. 7(a)-7(c) are graphs showing normal and critical sites that are selected to track stress/strain variations in the plaque sample of FIGS. 4(a)-4(c): P1, from calcification cap; P2, from a thicker Ca cap; P3, from a thicker Ca cap; P4, from a thin lipid core cap (most vulnerable site); P5, normal point to observe stress-xx; P6, normal point to observe stress-yy.
Figure 8:
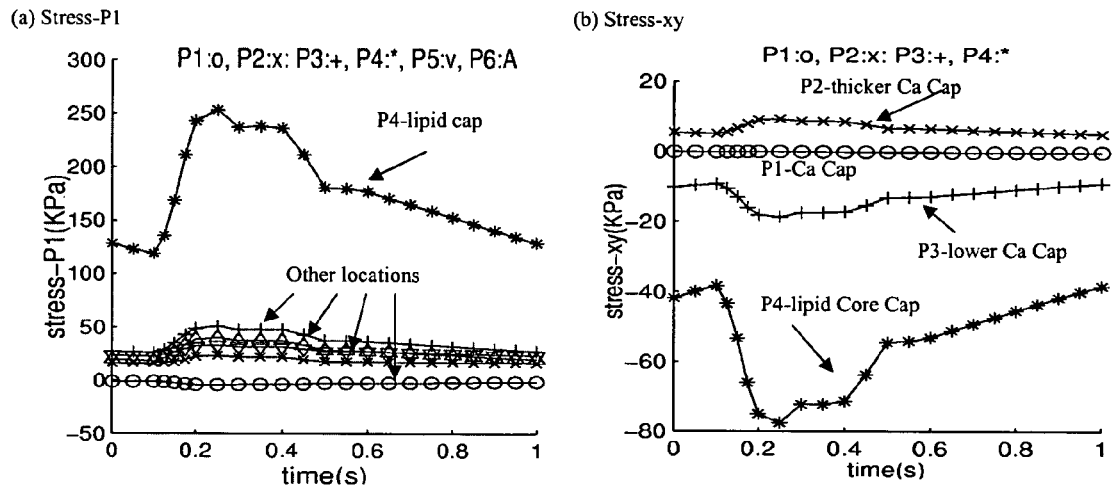
FIGS. 8(a) and 8(b) are graphs showing tracking of stress components at selected locations under pulsating pressures showing critical point from a thin lipid core cap has much greater stress variations: (a) Stress-P1 plots showing stress variation at the thin lipid core cap is much higher (400%) than that at other locations; (b) Stress-xy (shear stress) plots showing that shear stress variation at the thin lipid core cap is much higher (400%) than that at other locations.

Blood flow is pulsatile. Thus, blood vessel and atherosclerotic plaque are subjected to strong pulsating pressure conditions. Accordingly, unsteady stress/strain behaviours at critical sites under pulsating pressure were studied under the hypothesis that relative stress/strain variations in the plaque under pulsating pressure might correlate with plaque rupture risk. Since unsteady 3D stress/strain (both were tensors, each had 6 components) behaviours were extremely complex, and plaque structure was adding difficulty to the investigation, in this study, a "critical site tracking" approach was used to perform initial analysis. Using the plaque sample given by FIGS. 4(a)-4(c) and pressure conditions given by FIGS. 5(a)-5(b), several critical sites were selected from various locations (see FIGS. 7(a)-7(c)) to observe stress/strain variations under various conditions. Plots of Stress-$P_1$ and Stress-xy (shear component) from one cardiac cycle at 6 selected locations were given in FIGS. 8(a)-8(b) which showed that stress at the thin cap location (P4) had much greater (>400%) variation than that at other locations. These initial results indicate that stress/strain variations carry useful information for providing assessment for plaque vulnerability to rupture.

1B.3 More Severe Stenosis Leads to Lower Plaque Stress Level

Figure 5:
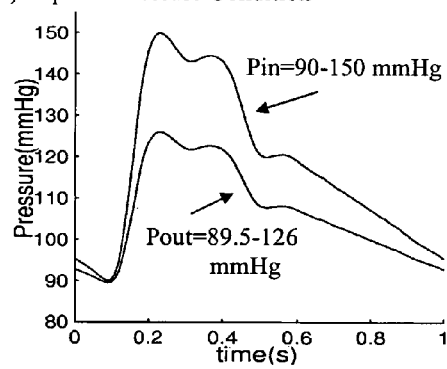
FIGS. 5(a) and 5(b) show prescribed pressure conditions for baseline models of the invention and corresponding flow rates: (a) a typical pressure profile for human internal carotid scaled to 90-150 mmHg and used as an upstream pressure ($P_{in}$) where down stream pressures ($P_{out}$) are chosen so that the corresponding flow rates are within physiological ranges; (b) Flow rate corresponding to the prescribed pressure conditions of FIG. 5(a).
Figure 5:
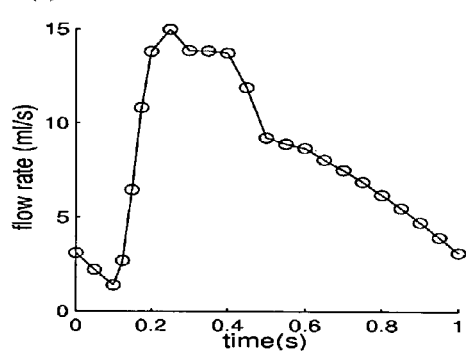
Figure 9:
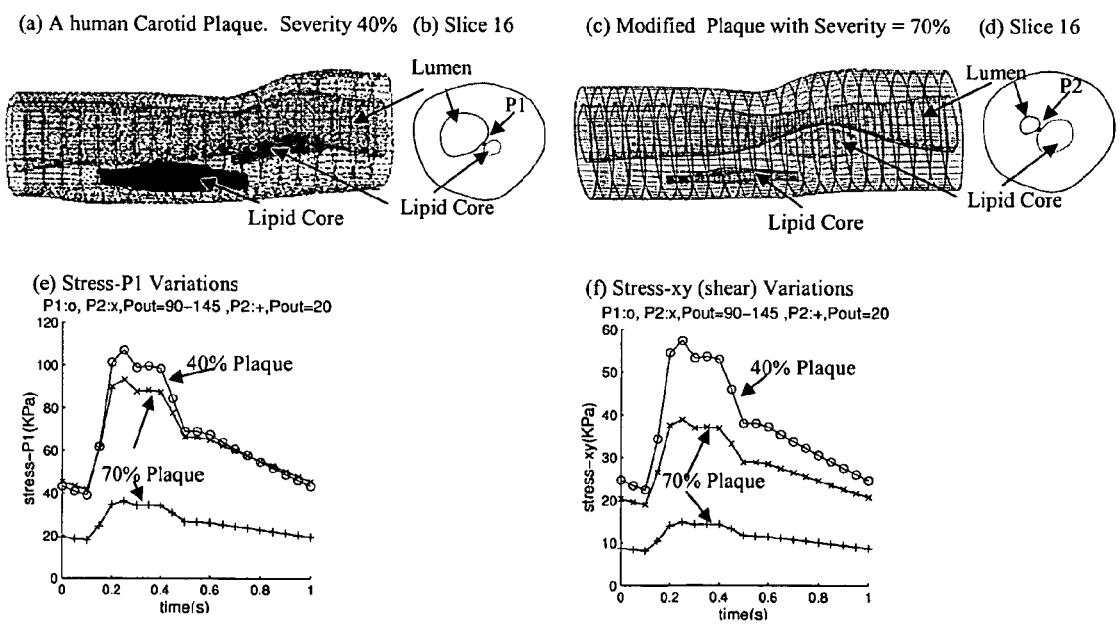
FIGS. 9(a)-9(d) show plaque models of the invention: (a) A human carotid plaque with 40% stenosis severity (by diameter); (b) Cross-sectional view of slice 16 of the model of FIG. 9(a), showing tracking position P1; (c) modified plaque with 70% stenosis severity (by diameter); (d) Cross-sectional view of slice 16 of the model of FIG. 9(c), showing tracking position P2.
FIGS. 9(e) and 9(f) are graphs showing stress-P1 variations and stress-shear variations, respectively, for three cases using the 3D models of FIGS. 9(a) and 9(c): Case 1: A human carotid plaque with 40% stenosis severity (FIG. 9(a)), $P_{in}$=90-150 mmHg, $P_{out}$=90-145; Case 2: A modified plaque with 70% stenosis severity (FIG. 9(c)), pressure: same as Case 1; Case 3: Same plaque as in Case 2, $P_{in}$=90-150 mmHg, $P_{out}$=20 mmHg (Axial stretch=10% for all three cases).

To investigate and demonstrate this important stress behaviour further, simulations were carried out using two sets of models: one constructed from a real human carotid plaque, and one based on a series of in vitro stenosis models (Tang, et al, *Annals of Biomedical Engineering*, 32(7), pp. 947-960 (2004) and Tang, et al., *J. Biomechanical Engineering*, 126, pp. 363-370 (2004)). FIG. 9(a) shows the geometry of a human carotid plaque re-constructed from MR images. The stenosis severity of this plaque was about 40% by diameter. FIG. 9(c) shows the geometry of a plaque modified from the real plaque so that plaque stenosis severity became about 70% by diameter, with other conditions and parameters kept the same. Two locations as indicated by $P_1$ and $P_2$ were selected to track stress/strain variations (see FIGS. 9(b) and 9(d)). Three cases were simulated. Upstream pressure was set using $P_{in}$=90-150 mmHg as shown in FIGS. 5(a)-5(b). Case 1 used 40% plaque sample with prescribed down stream pressure $P_{out}$=90-145 mmHg. The corresponding flow rate was between 1.74-21.08 ml·s$^{-1}$. Case 2 was for the modified 70% plaque with the same pressure conditions as in Case 1. Flow rate for this case became 0.2-4.4 ml·s$^{-1}$ due to increased severity. Case 3 was for the modified 70% plaque with downstream pressure fixed at 20 mmHg. Flow rate for this case became 8.65-14.16 ml·s$^{-1}$, closer to that in Case 1. Stress variations (Stress-P1 and Stress-xy) for the three cases are given in FIGS. 9(e) and 9(f). Stress-P1 peak value from Case 1 was about 200% higher than those from Case 3. Differences of Stress-xy peak values between the two cases were even greater (about 300%). Differences of stress peak values between Case 1 and Case 2 were about 20-50% where pressure conditions were the same for both cases.

Figure 10:
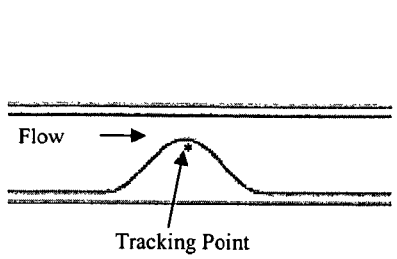
FIGS. 10(a) and 10(b) are simulations using in vitro models showing that higher stenosis severity leads to lower stress variations: (a) In vitro stenosis model and location of tracking point (Tube inner diameter=8 mm, tube wall thickness (straight part)=1 mm, tube length=140 mm, stenosis length=16 mm); (b) Plots of stress components at the tracking point vs. stenosis severity ($P_{in}$=150, $P_{out}$=145 (mmHg).
Figure 10:
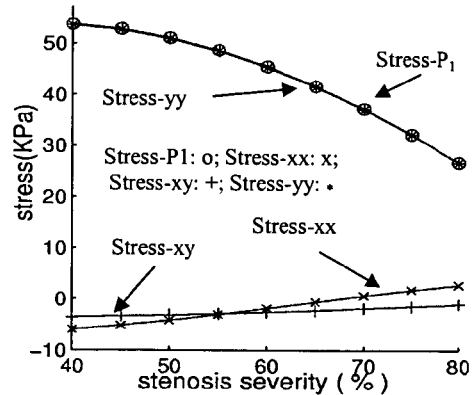

To simplify the problem a little further and to obtain more quantitative results, a series of simulations based on in vitro stenosis models was conducted and stress/strain values were tracked at a critical site (see FIGS. 10(a)-10(b)) to find a correlation between stress/strain behaviours and stenosis severity variations. FIG. 10(a) shows the geometry of a stenosis model. FIG. 10(b) shows plots of stress components at the tracking point from 9 severity cases ranging from 40% to 80% (by diameter), with 5% incremental change for each case. Upstream and downstream pressures were 150 mmHg and 145 mmHg, respectively, and were kept the same for all the 9 cases. As stenosis severity was reduced from 80% to 40%, Stress-P1 increased by about 100% (from 26 to 54 KPa).

1B.4 Plaque Lipid Core Cap and Location of Maximal Stresses.

Figure 11:
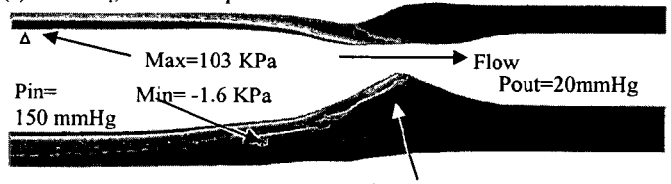
FIGS. 11(a) and 11(b) are computational band plots of Strss-P1 on sagittal cuts of vessels with cap thickness of 0.8 mm and 0.02 mm, respectively, showing that a thinner plaque cap leads to a higher stress level: (a) Stress-P1 at a thin, healthy site of plaque with a thicker cap (0.8 mm); (b) maximum of Stress-P1 at a thin plaque cap (0.02 mm).
FIG. 11(c) is a graph of maximal stress values tracked at the plaque cap of FIGS. 11(a)-11(b), showing that maximal values of Stress-P1 increases almost exponentially when cap thickness decreases: 11 simulated cases using the 70% modified plaque sample with cap thickness adjusted incrementally from 0.02 mm to 0.42 mm with $P_{in}$=150 mmHg and $P_{out}$=20 mmHg.
Figure 11:
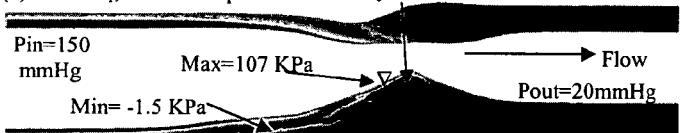
Figure 11:
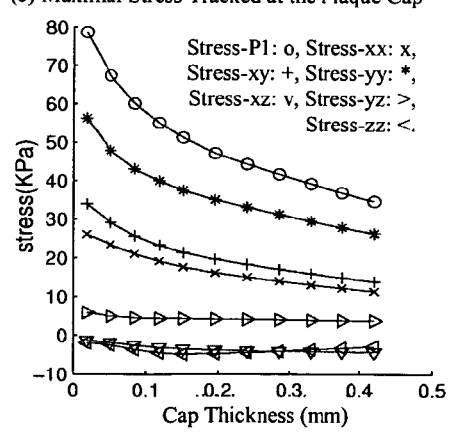

It is generally known that lipid core and its cap thickness have considerable effect on stress distributions and extreme stress locations (critical points). 70% plaque (FIG. 9(c)) was chosen for this case study. FIGS. 11(a)-11(b) show band plots of Stress-$P_1$ on a sagittal cut of the vessel with cap thickness 0.8 mm and 0.02 mm, respectively. Maximal Stress-$P_1$ appeared at the thin (healthy) side when cap thickness was greater than 0.04 mm and moved to the cap site when the cap was adjusted thinner (=0.02 mm for the case shown). FIG. 11(c) shows stress values at the tracking point (FIG. 9(d)) for 11 cases with cap thickness adjusted incrementally from 0.42 mm to 0.02 mm. Stress-P1 values increased about 100% corresponding to the cap thickness variations. Other stress components showed similar patterns.

1B.5 Erosion

Figure 12:
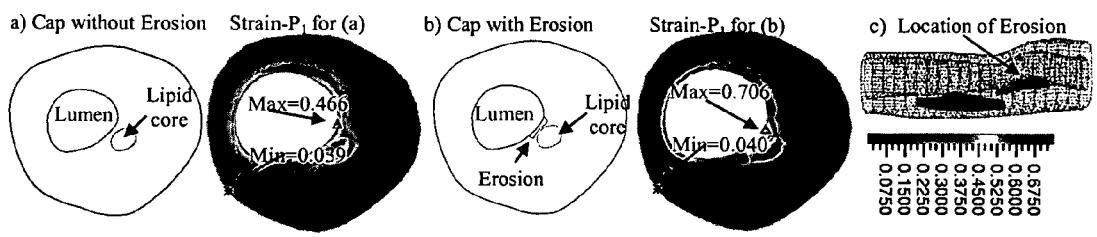
FIGS. 12(a)-12(c) are computer simulations of plaque of FIGS. 9(a)-9(d), showing that plaque cap erosion/weakening causes large strain increase: (a) maximum and minimum strain-P1 for plaque cap without erosion; (b) maximum and minimum strain-P1 plague cap with erosion; (c) location of erosion.

Cap erosion and inflammation generally weaken vessel surface (plaque cap) and may lead to large strain variations. Using the plaque given in FIGS. 9(a)-9(d), we made half (in cap thickness) of plaque cap softer to represent cap erosion (stiffness was reduced by 50%). For the plaque with cap erosion, maximal stress value changed less than 1%. FIGS. 12(a)-12(c) show that maximum of maximal principal strain (Strain-$P_1$) increased about 50% due to the cap weakening. These results confirm that cap erosion and inflammation are generally closely related to plaque rupture risk.

1B.6 Effect of Material Properties of Vessel and Plaque Components on Stress Behaviors.

Figure 13:
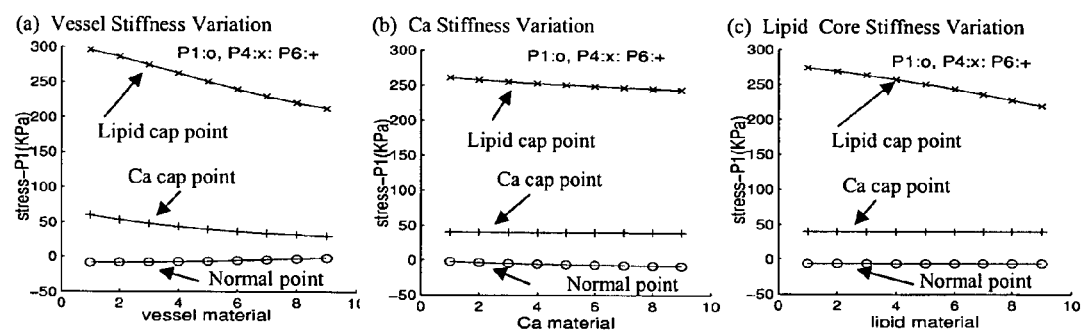
FIGS. 13(a)-13(c) are graphs showing plots of Stress-P1 at three selected points with different material parameters showing that material properties have considerable effect on stress distributions; $P_{in}$=150 mmHg, $P_{out}$=126 mmHg, axial-stretch=10%. (a) Vessel stiffness variations: c1=60,000-124,000; D1=20,000-52,000; D2=1.6-2.4; Ca and lipid used baseline values; b) Ca stiffness variations: c1=600,000-1,240,000; D1=200,000-520,000; D2=1.6-2.4; vessel and lipid used baseline values; c) Lipid core stiffness variations: c1=3,400-6,600; D1=3,400-6,600; D2=1.1-1.9; vessel and Ca used baseline values.

Using the plaque sample shown in FIGS. 4(a)-4(c), starting from the material parameters used in the baseline model, material parameters for vessel, calcification and lipid-rich core were varied (changing one material parameters while holding the other two unchanged) incrementally within a specified range. Plots of stress-$P_1$ values from three selected points are shown in FIGS. 13(a)-13(c). P1 was chosen from a calcification cap location, P4 was chosen from a lipid core cap location, and P6 was chosen from a "normal" (healthy) location. Stress-$P_1$ at the lipid cap decreased by about 30% (or a 50% increase) with a 100% vessel stiffness increase (or a 50% stiffness decrease), decreased 6% with 100% calcification stiffness increase, and decreased by 18% with 100% lipid core stiffness increase. Changes at other two locations were much less noticeable. Table 1 gives more information for maximal values of all the stress components from two cross-sectional cut slices for several cases. Percentage differences were much higher when individual components were examined. The quantitative study indicates that obtaining accurate material property information is helpful for the accuracy of computational simulations. Plaque structure and component size were also important factors. Direct measurements of vessel and plaque mechanical properties would be very desirable and improve accuracy and reliability of computational findings.

TABLE 1

Maximum stress values (Unit: KPa) from Slice 20 and Slice 4 of a large calcification plaque sample (slice 4 did not include a large lipid pool): Case 1: Baseline material, 5% stretch; Case 2: Softer vessel; Case 3: Stiffer vessel; Case 4: Baseline material, 10% Stretch; Case 5: S4, baseline, no lipid.

| Cases | S-P1 | S-xx | S-xy | S-xz | S-yy | S-yz | S-zz |
|---|---|---|---|---|---|---|---|
| Case 1: | 245 | 231 | 161 | 3.3 | 150 | 11.2 | 79.3 |
| Case 2: | 373 | 355 | 266 | 4.9 | 288 | 16.0 | 94 |
| Case 3: | 187 | 172 | 85 | 3.6 | 75 | 9.4 | 69.4 |
| Case 4: | 247 | 229 | 161 | 4.4 | 146 | 13.9 | 107 |
| Case 5: | 259 | 241 | 82 | 6.0 | 51 | 6.4 | 51 |

1C.1 Model Assumptions

Compared to MRI-based plaque models in the current literature, the 3D models of this example included fluid-structure interactions and 3D multi-component plaque structures into the model. The 3D models of this example were more of "free standing" models in the sense that both carotid and coronary arteries were modeled as standing-alone pieces, with only axial stretch applied. Also, in this example, the local stress/strain analysis was focused on, based upon the hypothesis that a plaque rupture would be more directly related to structural forces.

1C.2 Sensitivity Analysis and Critical Site Tracking Approach.

One difficulty for plaque stress/strain analysis of the invention was that a huge amount of data needs to be analyzed in order to find correlations between the amount of data that could be collected and measured, or calculated, and the end-point data based on which assessment for plaque vulnerability could be predicted. The list of controlling factors consisted of plaque and vessel morphological features, material properties (including vessel and plaque components), flow environment, modeling assumptions, and many others. Stress/strain solutions (excluding flow quantities) consist of 12 components, all time-dependent, 3D with complex structures. To reduce the number of controlling factors, simulation schemes were designed so that one factor was varied incrementally while other conditions were kept unchanged. These single-factor results can be helpful for further multi-factor analysis when all samples are from real patients and various factors jointly affect the stress/strain behaviors. To reduce the amount of data to examine, the CST approach was utilized. Rather than searching over the entire 3D domain, only those critical sites that covered all possible rupture candidates were examined.

The sensitivity analysis of this example and critical site tracking analysis indicate that vessel and plaque material properties, plaque structure, component volume and pressure conditions have large impact on stress/strain behaviours. Considerably higher stress/strain variations under pulsating pressure were observed at thin plaque cap.

Example 2

Local Maximal Stress Hypothesis and Computational Plaque Vulnerability Index (CPVI) for Atherosclerotic Plaque Assessment In Example 1, a 3D MRI-based computational model with multi-component plaque structure and fluid-structure interactions (FSI) was introduced to perform mechanical analysis for human atherosclerotic plaques and identify critical flow and stress/strain conditions which may be related to plaque rupture. In this Example 2, a "local maximal stress hypothesis" and a stress-based computational plaque vulnerability index (CPVI) were used to assess plaque vulnerability. Local maximal stress results tracked at critical sites in the plaque were be used to determine CPVI values. A semi-quantitative histopathological method was used to classify plaques into different grades, according to factors which were generally known to correlate with plaque vulnerability. This histopathological classification was used as the "gold standard" to validate the computational indices of this example. 34 human coronary plaque samples (2D slices) were studied and our CPVI index showed an impressive 85% agreement rate with histopathological classifications.

2A Models and Methods

2A.1 The Solid and Fluid Models

3D FSI models in this example were prepared by the method described in Example 1 using equations of (1)-(12) described above. For the 3D FSI models, blood flow was assumed to be laminar, Newtonian, viscous and incompressible. The incompressible Navier-Stokes equations with arbitrary Lagrangian-Eulerian (ALE) formulation were used as the governing equations which are suitable for FSI problems with frequent mesh adjustments. Both artery vessel material and plaque components in the plaque were assumed to be hyperelastic, isotropic, incompressible and homogeneous. No-slip conditions and natural traction equilibrium conditions were assumed at all interfaces. The 3D nonlinear modified Mooney-Rivlin (M-R) model was used to describe the material properties of the vessel wall and plaque components. The strain energy function was given by equation (9) above. In this example, the following values were chosen for the baseline models: vessel material: $c_1$=92,000 dyn·cm$^{-2}$, $c_2$=0, $D_1$=36,000 dyn·cm$^2$, $D_2$=2; lipid-rich core: $c_1$=5,000 dyn·cm$^{-2}$,$c_2$=0, $D_1$=5,000 dyn·cm$^{-2}$, $D_2$=1.5; calcification: $c_1$=920,000 dyn·cm$^{-2}$, $c_2$=0, $D_1$=360,000 dyn·cm$^{-2}$, $D_2$=2.

For 2D models, cross-sectional MRI images were used to get the geometries. The solid model and material parameters were the same as those used in the 3D FSI model. Lumen pressure was imposed to obtain stress/strain distributions in the plaque. No flow was involved in these 2D models because only one cross-section of the plaque was taken. In these 2D models, no pressure gradient could be prescribed. Even though 2D models were more simplified than 3D models, relative differences of stress/strain values from different plaques could still be used for quantitative plaque assessment. In this example, 2D plaque samples were used to obtain some preliminary data which could be extrapolated to 3D models.

2A.2 Fixation Procedures and Histopathological Plaque Vulnerability Index (HPVI)

This study was conducted mainly based on 2D MRI slices obtained from human coronary plaque samples, with a few 3D samples used. 34 2D MRI images of coronary artery plaques were collected from 14 autopsy patients (10M, 4F, aged 60±15 years). Six patients died of coronary artery disease (CAD). For ex vivo 2D MRI images, resolution was 0.1×0.1 mm$^2$ for the first 18 cases, and 0.055×0.055 mm$^2$ (FOV=28 mm×28 mm, Matrix=512×512) for the last 16 cases. All specimens were fixed in a 10% buffered formalin solution and placed in a polyethylene tube. They were stored at 4° C. within 12 hours after removal from the heart. MRI imaging was taken within 2 days at room temperature.

Figure 14:
FIGS. 14(a)-14(d) are histological (left) and MR (middle) images and segmented contour plots (right) of selected sample plaques with various degrees of vulnerability as classified by histopathological analysis with critical sites indicated by "X": a) a remarkable stable plaque used as the baseline case; b) a well-caped stable plaque, V=1; c) an unstable plaque with a large lipid core and thin cap; d) a vulnerable plaque with a huge lipid-rich necrotic core, a separate Ca (calcification) deposit, and a very thin cap near lumen with many inflammatory cells.
Figure 14:
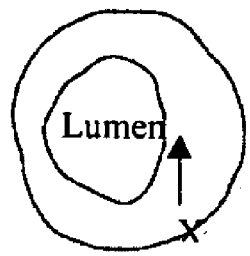
Figure 14:
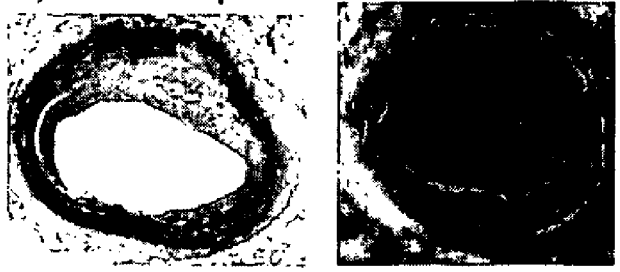
Figure 14:
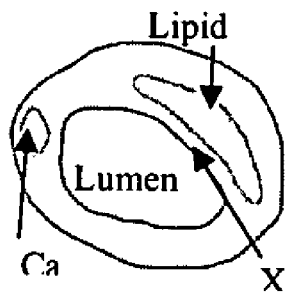
Figure 14:
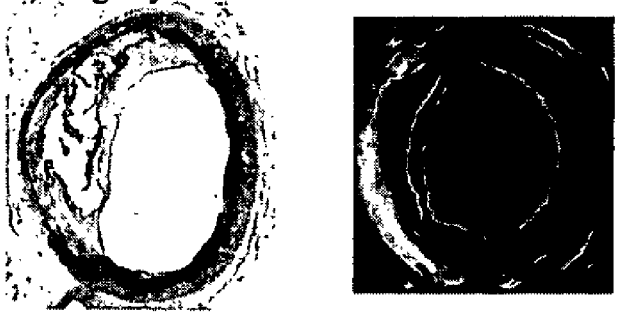
Figure 14:
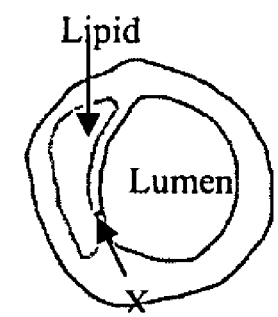
Figure 14:
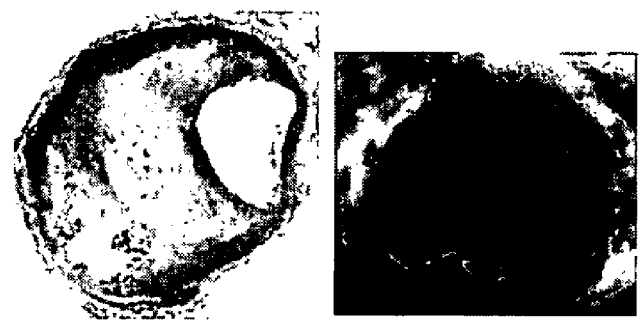
Figure 14:
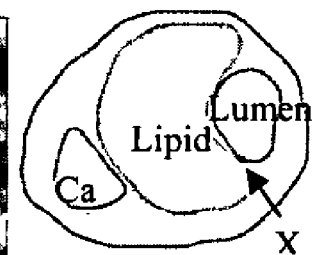

After completion of MR study, the transverse sections with a thickness of 5 μm were obtained at 0.5 mm intervals from each specimen. These paraffin-embedded sections were stained with hematoxylin and eosin (H&E), Masson's trichrome, and elastin van Gieson's (EVG) stains to identify major plaque components: calcification (Ca), lipid rich necrotic core (LRNC), and fibrotic plaques (FP). Sections were examined to characterize plaque structure and composition. The following Histopathological Plaque Vulnerability Index (HPVI) was used for plaque classifications and vulnerability assessment. HPVI values (denoted by V, ranging from 0-4) for atherosclerotic plaques were determined using a semi-quantitative analysis of structural features known to correlate with vulnerability. Features included were: a) the size and distribution of the soft lipid core; b) the fibrous capsule thickness; c) the number of macrophages and T-lymphocytes at the shoulders of the plaque and near the luminal interface; d) the number of smooth muscle cells. The HPVI class definitions and their comparisons with AHA (Association of Heart Attack) classifications are given in Table 2. Some plaque samples from different classes are given in FIGS. 14(*a*)-14(*d*). HPVI was used as the basis to establish computational plaque assessment schemes and validate computational findings.

TABLE 2

Histopathological plaque classifications and comparison with AHA classifications.

| HPVI Plaque | Description | AHA Classification |
|---|---|---|
| V = 0 Very stable | normal or slight intimal thickening | Class I, some atherogenic lipoprotein, adaptive intimal thickening |
| V = 1 Stable | moderate intimal thickening, no extra-cellular lipid, calcification or significant inflammation | Class II (fatty streak), III (preatheroma) |
| V = 2 Slightly Unstable | small lipid core (<30% of plaque size); calcification may be present; thick fibrous cap (>200 µm); little or no inflammation at plaque shoulders | Class IV, Vb, and Vc |
| V = 3 Moderately Unstable | moderate lipid core (30-40% of plaque size) and fibrous cap (65-200 µm); moderate intraplaque hemorrhage; moderate inflammation. | Class Va |
| V = 4 Highly Unstable | large lipid core (>40%); thin fibrous cap (<65 µm); large intra-plaque hemorrhage; extensive inflammation at plaque shoulders; evidence of previous plaque rupture | Class VI. |

2A.3 Segmentation and 3D Reconstruction

MRI data sets obtained from human atherosclerotic plaques with high resolution were read and segmented by a self-developed software package Atherosclerotic Plaque Imaging Analysis (APIA) written in Matlab (MathWorks, MATLAB, Natick, Mass.). All the segmented 2D slices were then read into ADINA® input file, pixel by pixel. ADINA® is a commercial finite element package (ADINA® R & D, Inc., Watertown, Mass., USA). Computational mesh was made using ADINA® automated mesh generation system. However, due to the complexity of plaque geometry, each plaque was divided into many "volumes" (ADINA® terminology) so that proper mesh could be chosen to fit the shape of each component, the vessel, and the fluid domain. Finer mesh was used for thin plaque cap and components with sharp angles to get better resolution and handle high stress concentration behaviours. Intensive interactions and additional programming from the operator/researcher were needed due to the complexity of plaque morphology and components. FIGS. 15(a)-15(e) show 2D coronary plaque slice sample and 3D plaque geometry re-constructed from 36 MRI slices of a cadaveric human coronary plaque sample with relatively high resolutions (0.1 mm×0.1 mm for 2D, 0.25 mm×0.23 mm×0.5 mm for 3D). The diameter of the 3D plaque sample was about 5-6 mm. MR image slice thickness was 0.5 mm. The total length of the vessel shown was 17.5 mm. Some smoothing (third-order spline) was applied to correct numerical and MR artifacts.

2A.4 Solution Method for the Computational Model

The 2D structure model and 3D fully coupled fluid and structure models were solved by ADINA® using unstructured finite element methods for both fluid and solid models, as described in Example 1.

2A.5 Assessing Plaque Vulnerability: CSS Method and CPVI

2A.5.1 The "Maximal Stress Hypothesis" May Be Misleading

FIGS. 16(a)-16(c), 17(a)-17(b) and 18 show that global maximal stress often appeared at healthy parts of the vessel where either vessel wall was thinner than the diseased plaque side or vessel curvature was large. These results indicated that maximal stress hypothesis, a current hypothesis in the literature that maximal stress may be related to possible plaque rupture and may be used for plaque vulnerability assessment, may not able to provide reliable mechanical plaque vulnerability.

In general, stress distributions in atherosclerotic plaques were affected by many factors which included (but were not limited to): a) Blood pressure which is the driving force of flow and vessel deformation. b) Vessel and plaque geometry. Vessel thickness and lumen area were both important. Thicker wall can typically lead to lower stress in the structure. Narrower lumen area can typically reduce the total fluid force acting on the structure and also can lead to lower stress in the plaque. c) Plaque structure. Multi-component structure can make the solid part non-homogeneous. d) Material properties of the vessel and plaque components. e) Fluid wall shear stress. f) Axial pre-stretch and residual stresses if included in the model. g) Inflammation and erosion. Blood pressure in severely stenosed artery was very non-uniform as indicated by the studies in Example 1. At the throat of the plaque (narrowest part of the lumen), pressure was lower due to high velocity there. In addition to that, the vessel wall (which included artery and plaque material) was much thicker in the plaque region. Lumen area was reduced. Those factors led to lower stress in the plaque region. That was probably why maximal stress was often observed at the healthy part of the vessel when the healthy side of the vessel was much thinner than the diseased side (FIGS. 16(a)-16(c), 17(a)-17(b) and 18). On the other hand, a large lipid pool and very thin plaque cap could change that. Global maximal stress could be observed at plaque cap if the cap became very thin and the lipid core was large enough. The combination of plaque geometry, vessel thickness, plaque cap thickness and flow forces generally determined global maximal stress and its location.

2A.5.2 Proposing the Local Maximal Stress Hypothesis and CSS Method

Figure 16:
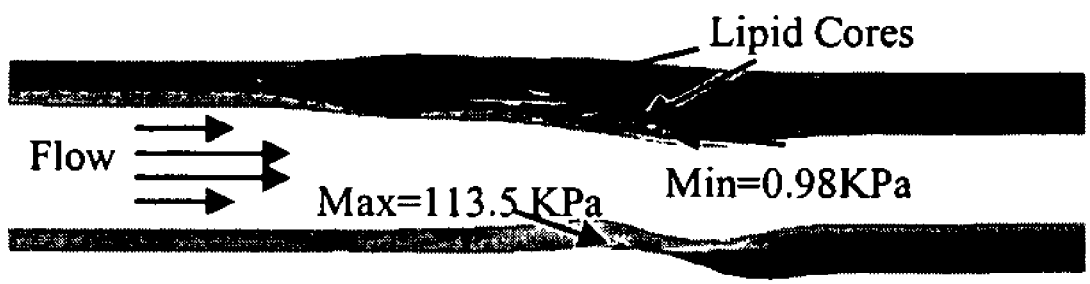
FIG. 16(a) is a computational band plot showing global maximal stress that appears at parts of the vessel where vessel wall is thinner than the diseased plaque side or the curvature is larger.
FIG. 16(b) is a computational band plot showing local maximal stress at locations where plaque rupture is more likely to occur.
FIG. 16(c) is a 3D computational model of the invention, which models the plaque of FIG. 16(a).
Figure 16:
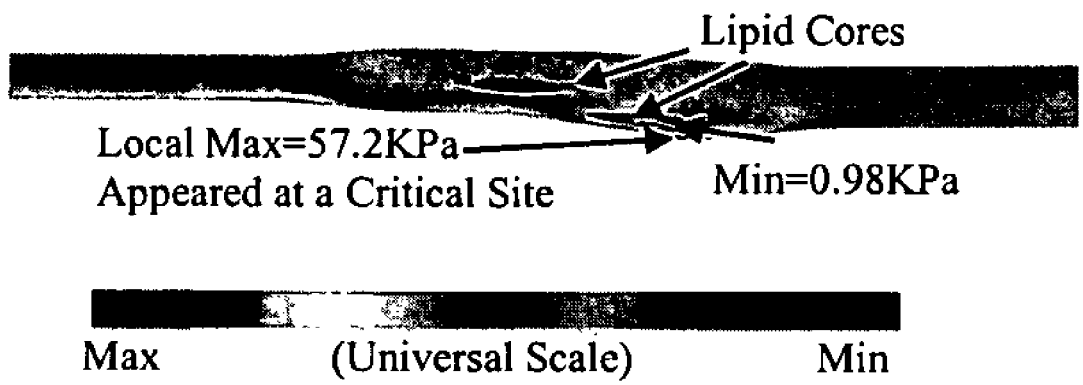
Figure 16:
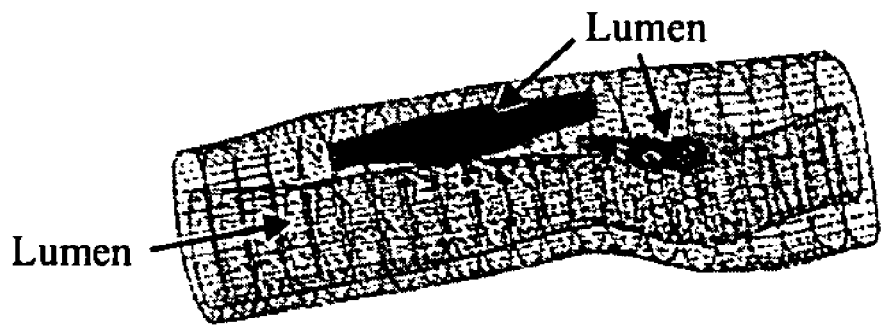
Figure 17:
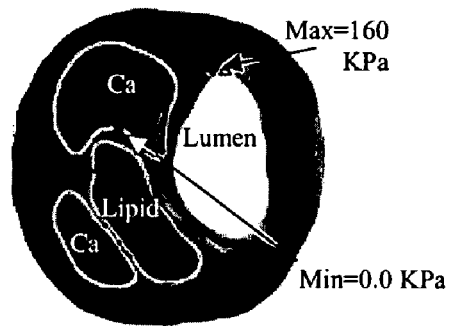
FIGS. 17(a) and 17(b) are 2D examples showing that global maximal stress often appears at healthy parts of the vessel where the curvature is larger (FIG. 17(a) or the vessel wall is thinner than the diseased plaque side (FIG. 17(b)).
Figure 17:
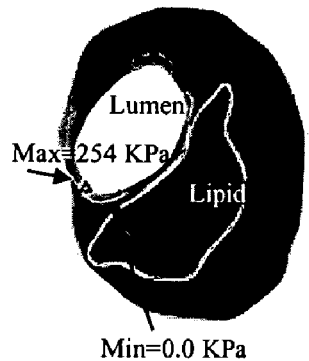
Figure 18:
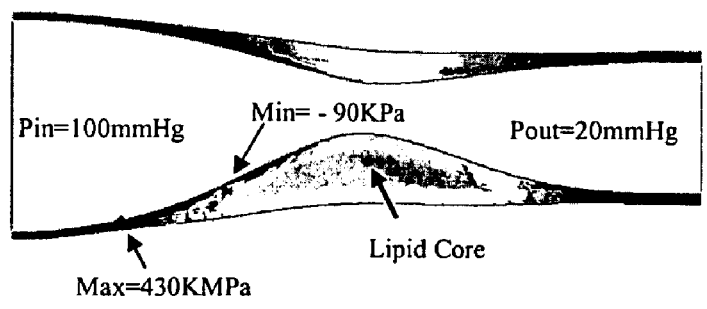
FIG. 18 is a 3D example based on in vitro experimental data showing global maximal stress at a healthy site where the vessel is thin.

For the above reasons, in this Example 2, local maximal stress/strain values and their variations were used for providing mechanical plaque vulnerability. FIG. 16(b) shows that a local maximal stress was found at the thin cap location where plaque rupture might be possible while the "maximal stress hypothesis" criterion missed this site (FIG. 16(a)). The "local maximal stress hypothesis" meant local maximal stress values at critical locations might be more closely related to possible plaque rupture and might be used for more accurate mechanical plaque assessment. Preliminary results are presented in next section to support this hypothesis.

Stress/strain conditions and locations which might be related to plaque rupture were called "critical stress/strain conditions" and "critical sites". A "critical site selection" (CSS) method was proposed to concentrate on plaque stress/strain behaviors at locations where local stress/strain maxima were found. These included locations of very thin cap, weakened cap sites, and other sites of special interest. Search for local maxima and their sites were programmed and made automatic. Stress/strain values at those sites were grouped by site category, analyzed by standard statistical methods, and the group showing best correlation with HPVI was chosen as the "critical site" (CS) stress/strain values. Critical sites which were clearly caused by fixation procedures and imaging artifacts were excluded from further statistical analysis. CSS method could reduce the full 3D search to the investigation of well-selected sites. Experience from physicians, radiologists, and pathologists could be combined with the computational techniques of the invention in the critical site selection process.

Figure 15:
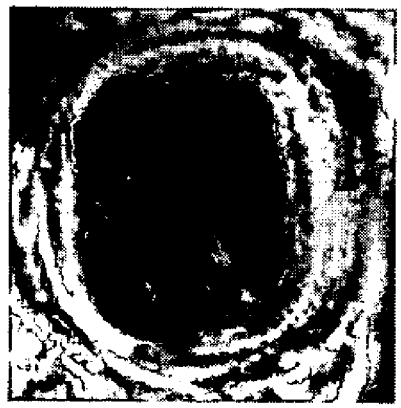
FIG. 15(a)-15(d) are 2D cadaveric human coronary plaque samples with large lipid cores and calcifications.
FIG. 15(e) is a 3D plaque geometry of the invention, which is reconstructed from 36 MRI slices of a cadaveric human coronary plaque sample.
Figure 15:
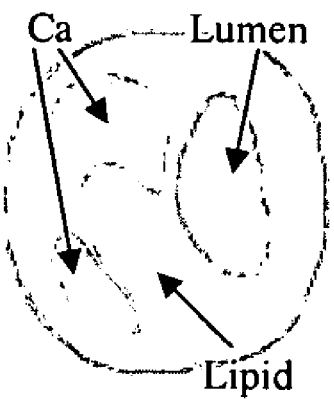
Figure 15:
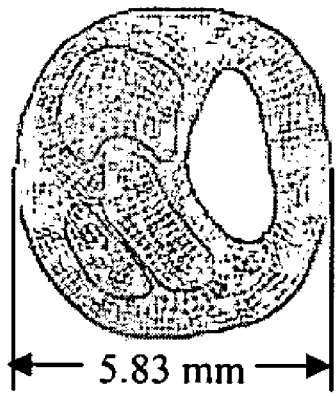
Figure 15:
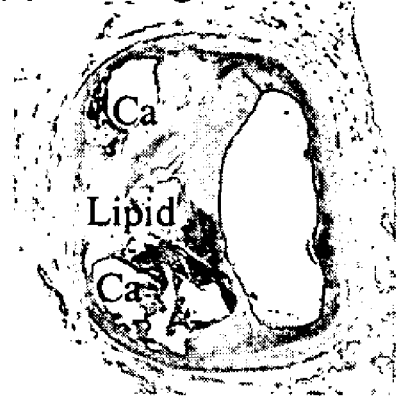
Figure 15:
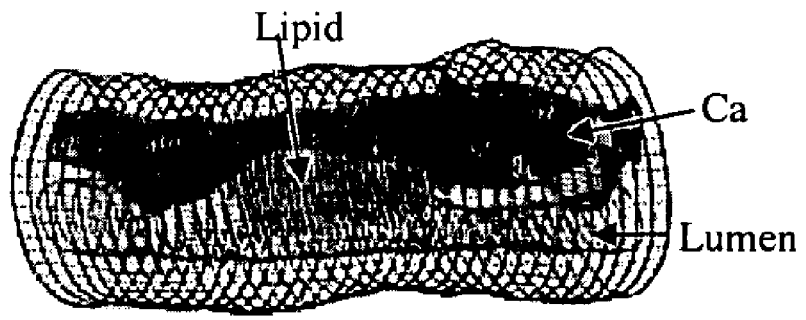
Figure 19:
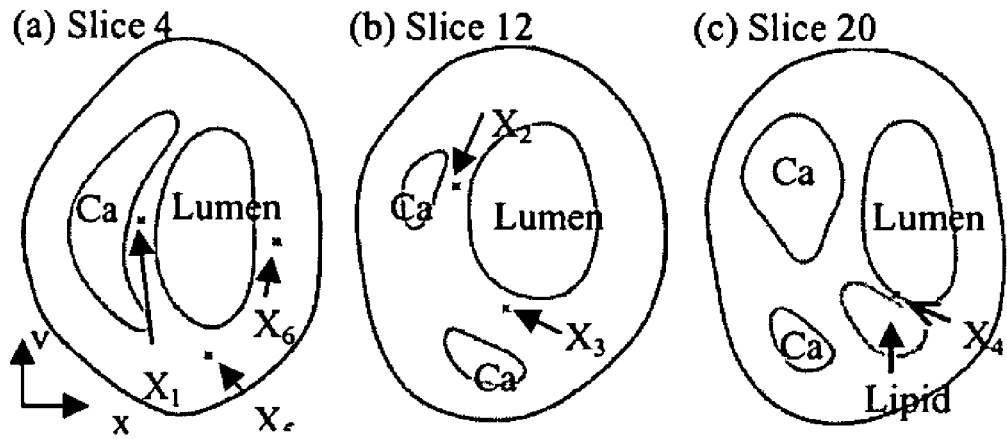
FIGS. 19(a)-19(d) show tracking of stress components at selected sites under pulsating pressure showing critical site at the thin lipid cap has much greater stress variations: (a-c) Normal and critical sites selected to track stress/strain variations. $X_1$: calcification cap; $X_2$: thicker Ca cap; $X_3$: thicker Ca cap; $X_4$: thin lipid cap (most vulnerable site); $X_5$: normal point to observe stress-xx; $X_6$: normal point to observe stress-yy; (d) Stress variation at the thin cap site is much greater (>400%) than that at other sites.
Figure 19:
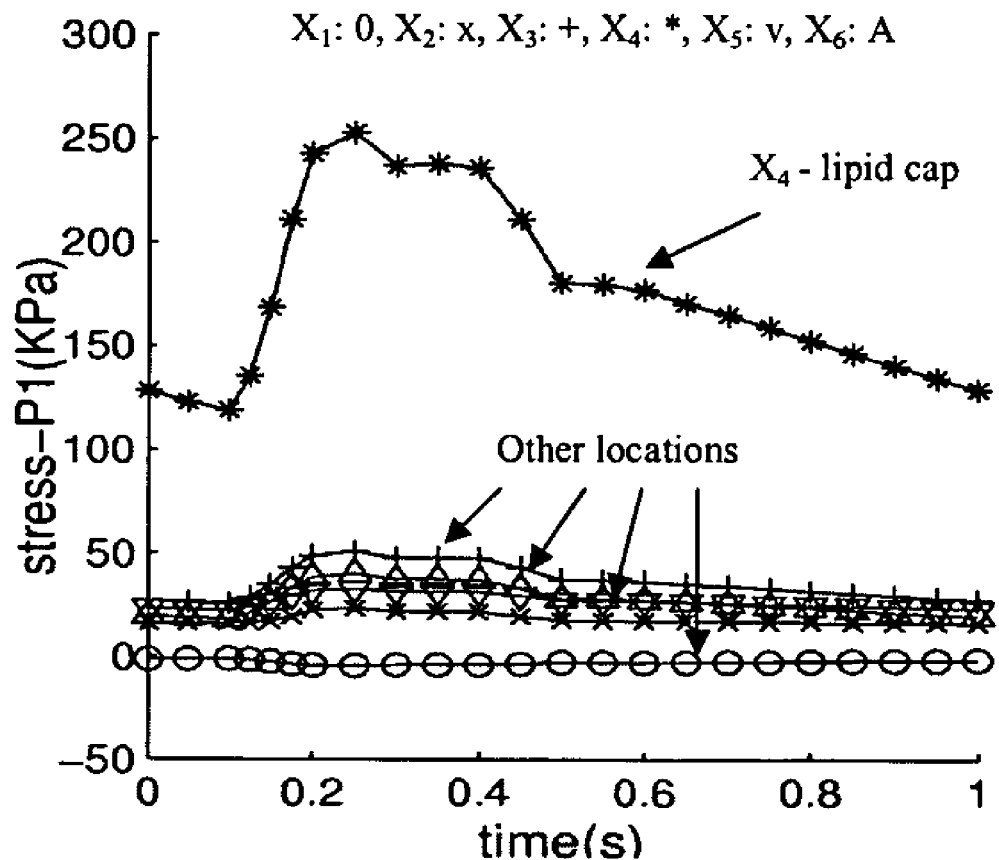

The 3D plaque sample given by FIG. 15(e) was used to demonstrate some preliminary results from a CSS method of the invention. Pulsating upstream pressure $P_{in}$=90-150 mmHg, downstream pressure $P_{out}$=89.5-126 mmHg were chosen to represent a typical high pressure case (see FIGS. 5(a)-5(b)). Corresponding flow rate was between 2-15 ml·s$^{-1}$. A 10% axial pre-stretch was applied. 6 sites were selected from various locations to observe stress/strain variations under various conditions (see FIGS. 19(a)-19(d)). Among them, $X_4$ was a critical site at the thin cap of a lipid core; $X_1$ and $X_2$ were located between the Ca block and lumen; $X_3$, $X_5$, and $X_6$ were less critical points serving as "control". As shown in FIG. 19(d), the thin cap location ($X_4$) had much greater (>400%) stress variation than other locations. This result shows a clear difference of stress behaviours between the critical site (thin cap over a large lipid core) and other non-critical sites.

2A 0.5.3 Introduction of Stress-Based Computational Plaque Vulnerability Index

Computational simulations were performed using plaque morphologies obtained from MRI images. Critical stress values (Stress-$P_1$ at selected critical sites corresponding to maximal pressure value from one cardiac cycle) were obtained using the CSS method for each of the samples. Statistical analysis using an ordinal multinomial generalized linear model (Agresti, Alan, *Categorical Data Analysis,* 2nd Edition, Wiley & Sons, New York, 2002, the entire teachings of which are incorporated herein by reference) was performed to quantify the relation between these CS Stress-$P_1$ values and plaque vulnerability as defined by HPVI. A stress-based computational plaque vulnerability index (CPVI, also ranging from 0-4) were assigned to each 2D slice sample evaluated according to the highest probability predicted by the statistical model. Stress intervals for all CPVI grades were also determined based on the data from the samples evaluated. Good agreement between CPVI and HPVI strongly indicated that the CPVI scheme can be used for clinical applications.

2B.1. CPVI Determined by an Ordinal Multinomial General Linear Model

Initial results were obtained from 34 MRI 2D slices from 14 autopsy patients (human coronary plaques) using 2D models under pulsating pressure conditions given in FIGS. 5(a)-5(b). Histological images of the plaques were examined to classify the vulnerability of these plaques. Histological and MR images of 4 selected plaques together with their segmented contour plots showing boundaries of various components and selected critical sites are given in FIGS. 14(a)-14(d). The site-selection procedure was explained in the previous section. Simulations were conducted under pulsating pressure (P=90-150 mmHg) and CS Stress-$P_1$ values corresponding to peak pressure were obtained for statistical analysis. Since the relationship between plaque vulnerability (HPVI) and CS Stress-$P_1$ was unknown (i.e., whether it was linear, nonlinear, or of any other type of relationship), an ordinal multinomial general linear model was fit to the data using CS Stress-$P_1$ as the predictor (see Agresti, Alan, *Categorical Data Analysis,* 2nd Edition, Wiley & Sons, New York, 2002, the entire teachings of which are incorporated herein by reference). In this model, CPVI grades were treated as ordinal numbers, i.e., their order was maintained, however, CPVI=4 did not mean that it was twice as much as CPVI=2. The fitted model took the form $$ln(C(k)/(1-C(k))=\mu(k)+\beta \cdot S, \qquad (13)$$

where S stands for CS Stress-$P_1$ which was used as the predictor. The probabilities C(k) in (13) were cumulative probabilities: i.e., $$C(k)=Prob(CPVI<=k). \qquad (14)$$

The individual probabilities which were computed from the fitted model (14) and used to decide the classification were given by, $$Pr(k)=C(k)-C(k-1), k=0-4, \text{ where } C(-1)=0 \text{ and } C(4)=1, \qquad (15)$$

$$Pr(k)=Prob(CPVI=k). \qquad (16)$$

The model was fit using the method of maximum likelihood, with the computations performed by the genmod procedure of SAS statistical software. The fitted parameter values along with standard errors and p-values (in parenthesis) were:
 β=−0.1568 (0.0473, p=0.0009),
 μ(0)=3.29 (1.12, p=0.0033), μ(1)=7.65 (2.20, p=0.0005),
 μ(2)=23.98 (7.80, p=0.0021), μ(3)=28.54 (8.86, p=0.0009).

Based on this model, estimates of the probabilities of each case taking on each of the possible HPVI values were computed (Table 3). The value k was assigned as the CPVI value for that plaque sample for which the estimated probability, Pr(k) was highest (see Table 3). CS Stress-$P_1$ results were from 2D models and were subject to modifications when 3D models were used and more plaque samples become available. Under CPVI vs. HPVI, 1=agree, 0=disagree. Disagreement for Plaque #8 was really marginal.

HPVI, CPVI, CS Stress-$P_1$ and the estimated probabilities (labeled Pr(0), Pr(1), Pr(2), Pr(3), and Pr(4)) for the 34 slice samples were listed and compared in Table 3. The agreement rate was about 85% which was fairly impressive. The agreement rate became 91% when the square root of CSST Stress-$P_1$ values was used in the statistical analysis procedure.

TABLE 3

Good agreement of CPVI with HPVI for plaque vulnerability assessment

| Plaque # | HPVI | CS Stress-$P_1$ | Pr(0) | Pr(1) | Pr(2) | Pr(3) | Pr(4) | CPVI | CPVI vs. HPVI |
|---|---|---|---|---|---|---|---|---|---|
| 1 | 0 | 10.20 | 0.84412 | 0.15353 | 0.00235 | 0.00000 | 0.00000 | 0 | 1 |
| 2 | 0 | 7.90 | 0.88594 | 0.11242 | 0.00164 | 0.00000 | 0.00000 | 0 | 1 |

TABLE 3-continued

Good agreement of CPVI with HPVI for plaque vulnerability assessment

| Plaque # | HPVI | CS Stress-$P_1$ | Pr(0) | Pr(1) | Pr(2) | Pr(3) | Pr(4) | CPVI | CPVI vs. HPVI |
|---|---|---|---|---|---|---|---|---|---|
| 3 | 0 | 4.04 | 0.93433 | 0.06477 | 0.00089 | 0.00000 | 0.00000 | 0 | 1 |
| 4 | 0 | 13.20 | 0.77185 | 0.22440 | 0.00375 | 0.00000 | 0.00000 | 0 | 1 |
| 5 | 0 | 15.10 | 0.71521 | 0.27974 | 0.00505 | 0.00000 | 0.00000 | 0 | 1 |
| 6 | 0 | 2.32 | 0.94907 | 0.05025 | 0.00068 | 0.00000 | 0.00000 | 0 | 1 |
| 7 | 1 | 28.60 | 0.23216 | 0.72741 | 0.04043 | 0.00000 | 0.00000 | 1 | 1 |
| 8 | 1 | 21.10 | 0.49499 | 0.49218 | 0.01283 | 0.00000 | 0.00000 | 0 | 0 |
| 9 | 1 | 25.60 | 0.32614 | 0.64822 | 0.02565 | 0.00000 | 0.00000 | 1 | 1 |
| 10 | 1 | 26.70 | 0.28942 | 0.68025 | 0.03033 | 0.00000 | 0.00000 | 1 | 1 |
| 11 | 1 | 40.60 | 0.04403 | 0.73929 | 0.21668 | 0.00000 | 0.00000 | 1 | 1 |
| 12 | 2 | 51.50 | 0.00827 | 0.38726 | 0.60447 | 0.00000 | 0.00000 | 2 | 1 |
| 13 | 2 | 48.30 | 0.01358 | 0.50582 | 0.48059 | 0.00000 | 0.00000 | 1 | 0 |
| 14 | 2 | 103.00 | 0.00000 | 0.00020 | 0.99940 | 0.00039 | 0.00000 | 2 | 1 |
| 15 | 3 | 171.00 | 0.00000 | 0.00000 | 0.05546 | 0.79291 | 0.15163 | 3 | 1 |
| 16 | 3 | 217.00 | 0.00000 | 0.00000 | 0.00004 | 0.00406 | 0.99590 | 4 | 0 |
| 17 | 4 | 185.00 | 0.00000 | 0.00000 | 0.00649 | 0.37730 | 0.61621 | 4 | 1 |
| 18 | 4 | 339.00 | 0.00000 | 0.00000 | 0.00000 | 0.00000 | 1.00000 | 4 | 1 |
| 19 | 4 | 204.50 | 0.00000 | 0.00000 | 0.00031 | 0.02813 | 0.97157 | 4 | 1 |
| 20 | 0 | 7.43 | 0.89318 | 0.10530 | 0.00152 | 0.00000 | 0.00000 | 0 | 1 |
| 21 | 2 | 137.00 | 0.00000 | 0.00000 | 0.92391 | 0.07523 | 0.00086 | 2 | 1 |
| 22 | 2 | 99.40 | 0.00000 | 0.00035 | 0.99942 | 0.00022 | 0.00000 | 2 | 1 |
| 23 | 0 | 22.50 | 0.44039 | 0.54368 | 0.01593 | 0.00000 | 0.00000 | 1 | 0 |
| 24 | 1 | 46.90 | 0.01686 | 0.55690 | 0.42624 | 0.00000 | 0.00000 | 1 | 1 |
| 25 | 0 | 2.29 | 0.94929 | 0.05003 | 0.00068 | 0.00000 | 0.00000 | 0 | 1 |
| 26 | 0 | 12.10 | 0.80080 | 0.19604 | 0.00316 | 0.00000 | 0.00000 | 0 | 1 |
| 27 | 0 | 13.00 | 0.77733 | 0.21904 | 0.00364 | 0.00000 | 0.00000 | 0 | 1 |
| 28 | 4 | 241.00 | 0.00000 | 0.00000 | 0.00000 | 0.00009 | 0.99990 | 4 | 1 |
| 29 | 4 | 174.80 | 0.00000 | 0.00000 | 0.03134 | 0.72376 | 0.24490 | 3 | 0 |
| 30 | 4 | 224.30 | 0.00000 | 0.00000 | 0.00001 | 0.00130 | 0.99869 | 4 | 1 |
| 31 | 4 | 317.20 | 0.00000 | 0.00000 | 0.00000 | 0.00000 | 1.00000 | 4 | 1 |
| 32 | 2 | 74.50 | 0.00023 | 0.01722 | 0.98255 | 0.00000 | 0.00000 | 2 | 1 |
| 33 | 1 | 24.90 | 0.35071 | 0.62625 | 0.02304 | 0.00000 | 0.00000 | 1 | 1 |
| 34 | 1 | 30.60 | 0.18097 | 0.76452 | 0.05451 | 0.00000 | 0.00000 | 1 | 1 |

Correspondence between CPVI grades and CS Stress-$P_1$ values as quantified by this procedure is given in Table 4. The intervals were sensitive to the number of cases considered and their HPVI distributions. The group with HPVI=3 was under-represented in this data set.

TABLE 4

CPVI and CS Stress-$P_1$ correspondence as quantified by the ordinal multinomial general linear model

| CPVI Value | CST Stress-P1 Range (KPa) |
|---|---|
| 0 | (0, 21.5) |
| 1 | [21.5, 48.65) |
| 2 | [48.65, 153.05) |
| 3 | [153.05, 181.85) |
| 4 | [181.85, 500+) |

2B.2 Linear Regression Analysis and the Pearson Product-Moment Correlation

Figure 20:
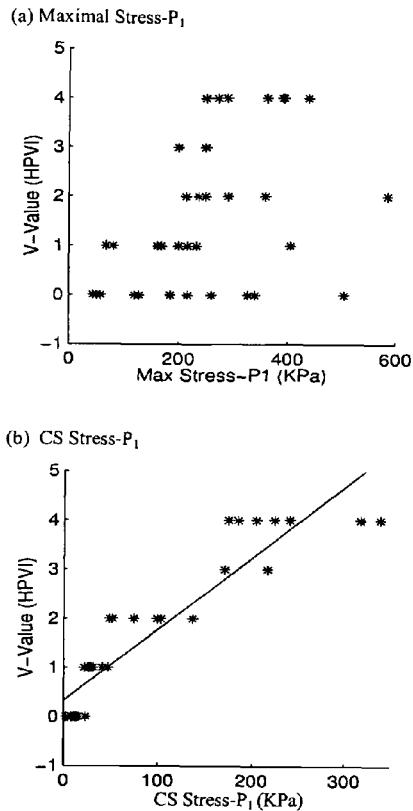
FIGS. 20(a) and 20(b) are graphs showing that stress-$P_1$ by CSS shows much better correlation with HPVI than global maxima of Stress-$P_1$ from 34 coronary 2D plaque samples (p<0.0001): (a) plots of HPVI values versus global maxima of Stress-P1; (b) plots of HPVI values versus local maxima of Stress-P1.
Figure 21:
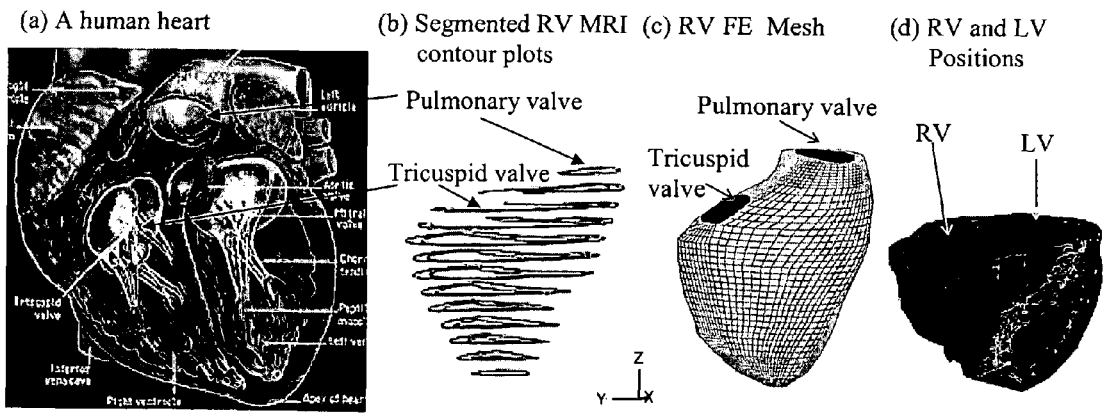
FIG. 21(a) is a figure showing a human heart.
FIG. 21(b) is a figure showing segmented right ventricle (RV) of the human heart of FIG. 21(a).
FIGS. 21(c) and 21(d) are computational 3D simulations of right ventricle (RV) of the human heart of FIG. 21(a).

Comparison between the global maxima of Stress-$P_1$ distribution and the CS Stress-$P_1$ values was given in FIGS. 20(a)-20(b), respectively. As shown in FIGS. 20(a) and 20(b), CS Stress-$P_1$ correlated much better with HPVI than global maxima of Stress-$P_1$. The linear function fitting the data by regression analysis (see FIG. 20(b)) was given by:

$$V = 0.3362 + 0.0145 * S, \quad (17)$$

where V was HPVI, and S stood for CS Stress-$P_1$. The correlation (Pearson product-moment correlation) between CS Stress-$P_1$ and HPVI was 0.92, which was highly significant (p-value<0.0001). A 99% confidence interval for the population correlation was (0.82, 0.97). In contrast, the correlation between global maximum stress and HPVI was 0.46, which, while significant (p-value=0.0125), was not highly significant. A 99% confidence interval for the population correlation was (−0.01, 0.72).

2C.1 Model Assumptions and Limitations.

The CPVI results were from 2D models based on 34 2D MRI slices from 14 patients while the corresponding histo-pathological data (HPVI) were used as the bench mark to quantify CPVI grades. When using 3D MRI data and 3D models, HPVI were determined for each slice, and the highest HPVI value from all the slices were picked as the HPVI grade for the plaque under consideration. The 3D stress/strain solutions were searched numerically to identify local maxima and their locations. Those sites were examined and critical sites and the associated stress/strain values were selected to be used for statistical analysis and CPVI assignment.

The preliminary results described above indicate that critical sites can be related to local morphologies which are less affected by the differences between ex vivo and in vivo morphologies. The CSS process also helped to eliminate some artifacts caused by fixation procedures and deformation of plaque samples.

2C.2 CPVI Validation, Gold Standard and Clinical Relevance

Histopathological analysis which typically regarded as the "gold standard" for validation of MRI tissue identification was used in this example as the gold standard for computational plaque assessment. HPVI was used as the bench mark to introduce and establish the stress-based CPVI of the invention. While postmortem histological sections had deformations from their in vivo shape, their critical features such as cap thickness, lipid pool size could be determined, with the help of MRI images taken before sectioning. Long-term patient tracking data with the actual plaque progression and rupture rate served as a better in vivo "gold standard." The results of this example provided initial evidence that computational plaque stress/strain analysis can lead to better quantitative predictions.

2C.3 Model Validation; Models Based on Histological, Ex Vivo and In Vivo Data

Computational model validations were performed based on in vitro experimental data in the studies of Example 1 and good agreement was found. In general, models based on histological sections are less accurate due to deformations from the fixation procedures. The computational modes of Example 1 were based on ex vivo MRI images and axial stretch (for 3D models), and pressurization (for 2D and 3D models) were added to recover the in vivo shape of the plaque computationally. For in vivo image-based models, the plaque geometry was shrunken to an estimated zero-stretch/zero pressure shape, then stretched and pressurized to get the correct initial stress/strain distributions in the plaque. This step could affect the computational stress predictions by as much as 400%-600% (see Tang, et al. "Sensitivity analysis of 3D MRI-based models with fluid-structure interactions for human atherosclerotic coronary and carotid plaques," Editor: K. J. Bathe, *Computational Solid and Fluid Mechanics*, Elsevier, New York, 2005, the entire teachings of which are incorporated herein by reference). Cardiac motion can have considerable effect on stress/strain distributions in coronary arteries and be added in the computational models of the invention.

2C.4 Selection of Indices and Multi-Dimensional Nature of Rupture Risk Assessment The CS Stress-$P_1$ values obtained by CSS method were used in this example to quantify CPVI. All stress/strain components, together with their variations under pulsating pressure used in the simulation (FIGS. 5(a)-5(b), $P_{in}$=90-150 mmHg) were examined. Stress/strain values at peak pressure ($P_{in}$=150 mmHg), their variations between the maximum (150 mmHg) and minimum pressures (90 mmHg), shear stress/strain components were obtained by CSS method for statistical analysis. It was found from the 34 cases that CS Stress-$P_1$ values had the best correlation with HPVI.

In general, vulnerability was material dependent and the absolute value of stress compared to material strength was an important factor. Results from the 3D models of the invention, together with extensive statistical analysis, can give more complete and accurate mechanical analysis. Predictions from mechanical side can be compared with predictions from other channels for comparisons and mutual enhancement.

Example 3

3D Image-Based Computational Modeling for Patient-Specific Mechanical Analysis of Human Hear Right Ventricles In this example, the MRI techniques and computational modeling were combined to build a patient-specific 3D computational model with fluid-structure interactions (FSI) for the human right ventricle (RV). Right ventricular dysfunction is one of the more common causes of heart failure in patients with congenital heart defects.

Due to the complexity of the motion of a human right ventricle and related blood flow and structure stress/strain behaviors, some simplifications were made in the modeling so that proper measurements could be obtained and the model could be solved to obtain flow and stress/strain information. Based on the solutions, mechanical analysis could be performed to analyze cardiac functions of the right ventricle. The patient-specific 3D computational modeling techniques of the invention can be further employed in computer-aided cardiac surgery planning to reach optimal design in patients with right ventricular dysfunction from congenital heart defects.

3A. Experiments

Figure 22:
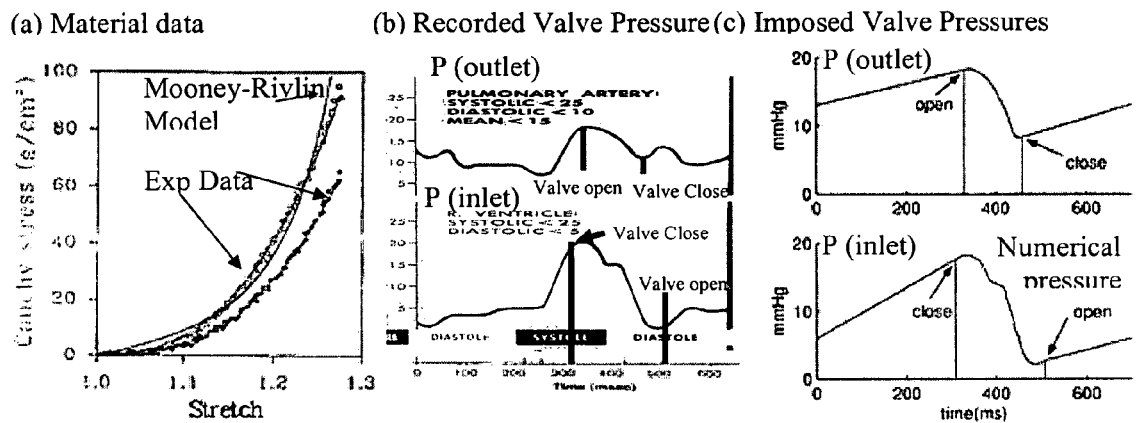
FIGS. 22(a)-22(c) are graphs showing experimental material data, Mooney-Rivlin stress-stretch curve, and pressure conditions prescribed at the in/out valves (parameters for Mooney-Rivlin Model matching experimental data: $c_1$=3600 dyn/cm², $D_1$=818 dyn/cm², $c_2$=0, $D_2$=12).

RV morphology and motion of a healthy human volunteer were acquired by using planar tagged MRI. Segmentation and 3D motion reconstruction were performed following procedures described in Example 1. 10 positions of the RV were acquired during one cardiac cycle, with each position containing 10-14 planar slices. 3D geometry of the RV and computational mesh (see FIGS. 21(a)-21(d) were constructed following the procedures described in Example 1 (see Tang, et al., *Annals of Biomedical Engineering*, 32(7):947-960 (2004)). The RV structure model assumed that the material to be hyperelastic, isotropic, nearly-incompressible and homogeneous. The nonlinear Mooney-Rivlin model was used to describe the nonlinear material properties of the muscle with parameters chosen to match experimental data available (FIGS. 22(a)-22(c)). The strain energy function for the modified Mooney-Rivlin model was given by (9) as described above.

The volume of computing cells changed when mesh was adjusted, obeying Geometry Conservation Law (GCL):

$$\text{Cell Volume}|_{new} - \text{Cell Volume}|_{old} = \int_v \nabla \cdot u \, dv \text{ (Geometry Conservation Law)} \quad (18).$$

ALE formulation and GCL enforcement were in general two critical techniques for successful algorithm implementation for problems involving free moving geometries. The flow was assumed to be laminar, Newtonian, viscous and incompressible. The Navier-Stokes equations with ALE formulation was used as the governing equations. Pressure conditions were prescribed at the tricuspid (inlet) and pulmonary (outlet) valves (see Kuehne T., et al, *Magnetic resonance imaging analysis of right ventricular pressure-volume loops*, Circ 110:2010-16 (2004), the entire teachings of which are incorporated herein by reference). Since RV muscle was treated as passive material, pressure conditions were modified so that RV could be inflated properly by fluid forces. No-slip boundary conditions and natural force boundary conditions were specified at all the interfaces to couple fluid and structure models together (see Bathe K. J., 1996, *Finite Element Procedures*. Prentice Hall, the entire teachings of which are incorporated herein by reference).

The coupled fluid and structure models were solved by a commercial finite-element package ADINA® (ADINA® R & D, Inc., Watertown, Mass.). Unstructured finite elements and the Newton-Raphson iteration method were used to solve the FSI model. Nonlinear incremental iterative procedures were used to handle fluid-structure interactions. Details for the models and solution methods are described in Example 1.

5B. Results

For this passive FSI model, the simulation cycle started when RV had its smallest volume corresponding to the minimal inlet pressure (t=480 ms). As the inlet pressure increases (inlet is kept open), blood flows into RV and its volume increases. When RV reached its maximal volume, tricuspid valve closed and pulmonary valves opened up. Blood got ejected out and RV volume decreased. That completed the cycle. While the mechanism driving the motion was different from the real heart, the simulated RV motion, deformation, and fluid flow similar to realistic cases with proper boundary conditions could be made.

Simulations were conducted under various pressure and material conditions, with variations in RV geometry and added patches to investigate the effects of potential diseases and surgeries may have on RV functions. Preliminary results are given below.

Figure 23:
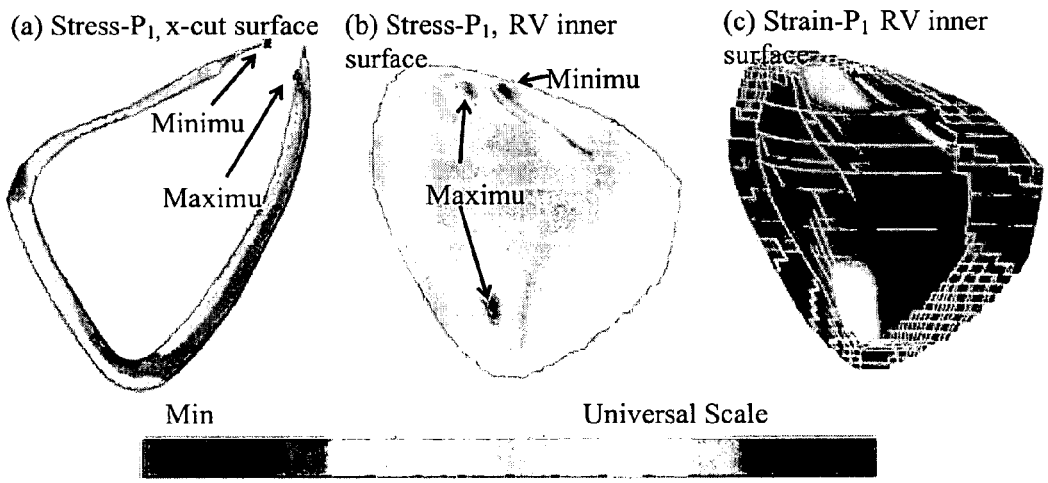
FIGS. 23(a)-23(c) are computer simulations of the RV, showing stress/strain distributions in the RV at t=0.3 s.
Figure 24:
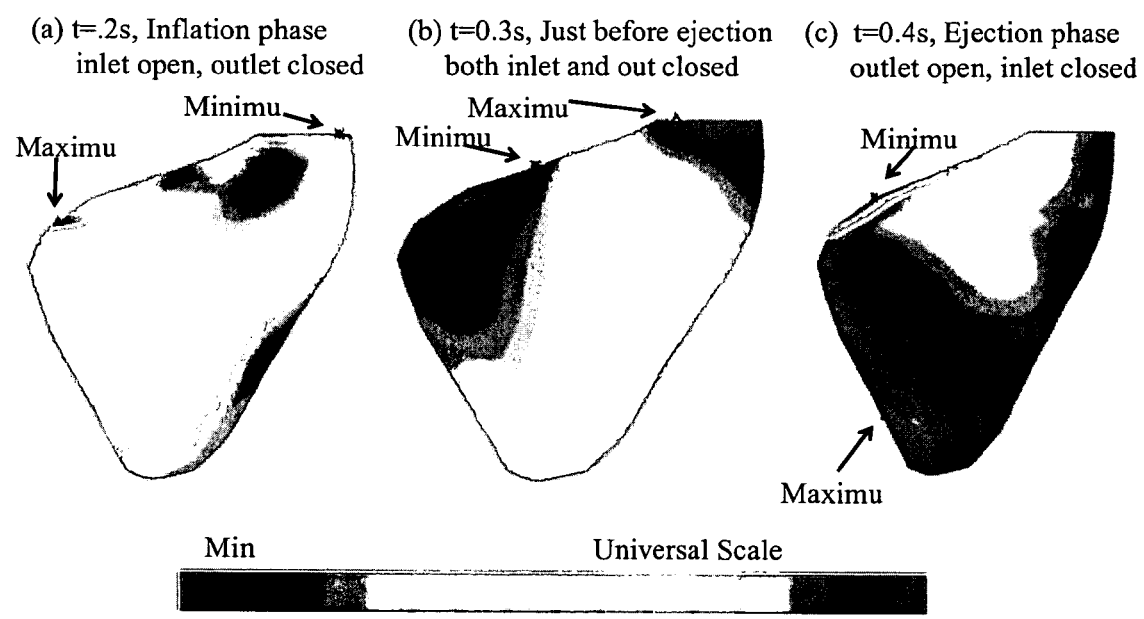
FIGS. 24(a)-24(c) are contour plots of pressure distributions on an x-cut surface at t=0.2 s, 0.3 s, and 0.4 s presented corresponding to the RV inflection, compression and ejection phases: (a) Inflation phase: pressure at inlet is specified to force flow into the RV chamber; (b) Compression phase: the RV is getting ready for ejection, and blood flow continues in the RV; (c) Ejection phase: the outlet valve is open.
Figure 25:
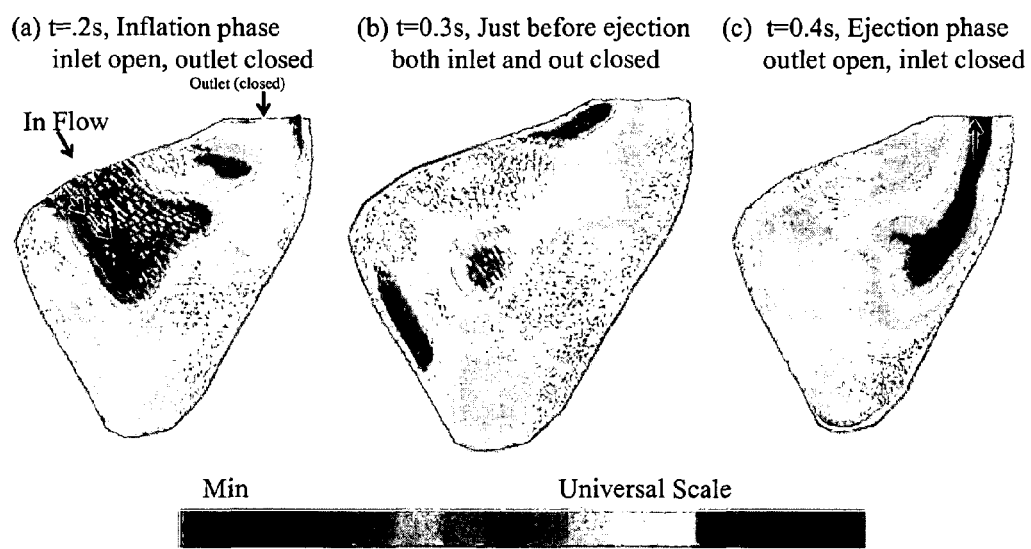
FIGS. 25(a)-25(c) are velocity plots on an x-cut surface at t=0.2 s, 0.3 s, and 0.4 s presented corresponding to RV inflection, compression and ejection phases: (a) Inflation phase: blood is entering the RV as forced by specified pressure; (b) Compression phase: the RV is getting ready for ejection, and blood flow continues in the RV; (c) Ejection phase: the outlet valve is open, and the blood is ejected from the RV.
Figure 26:
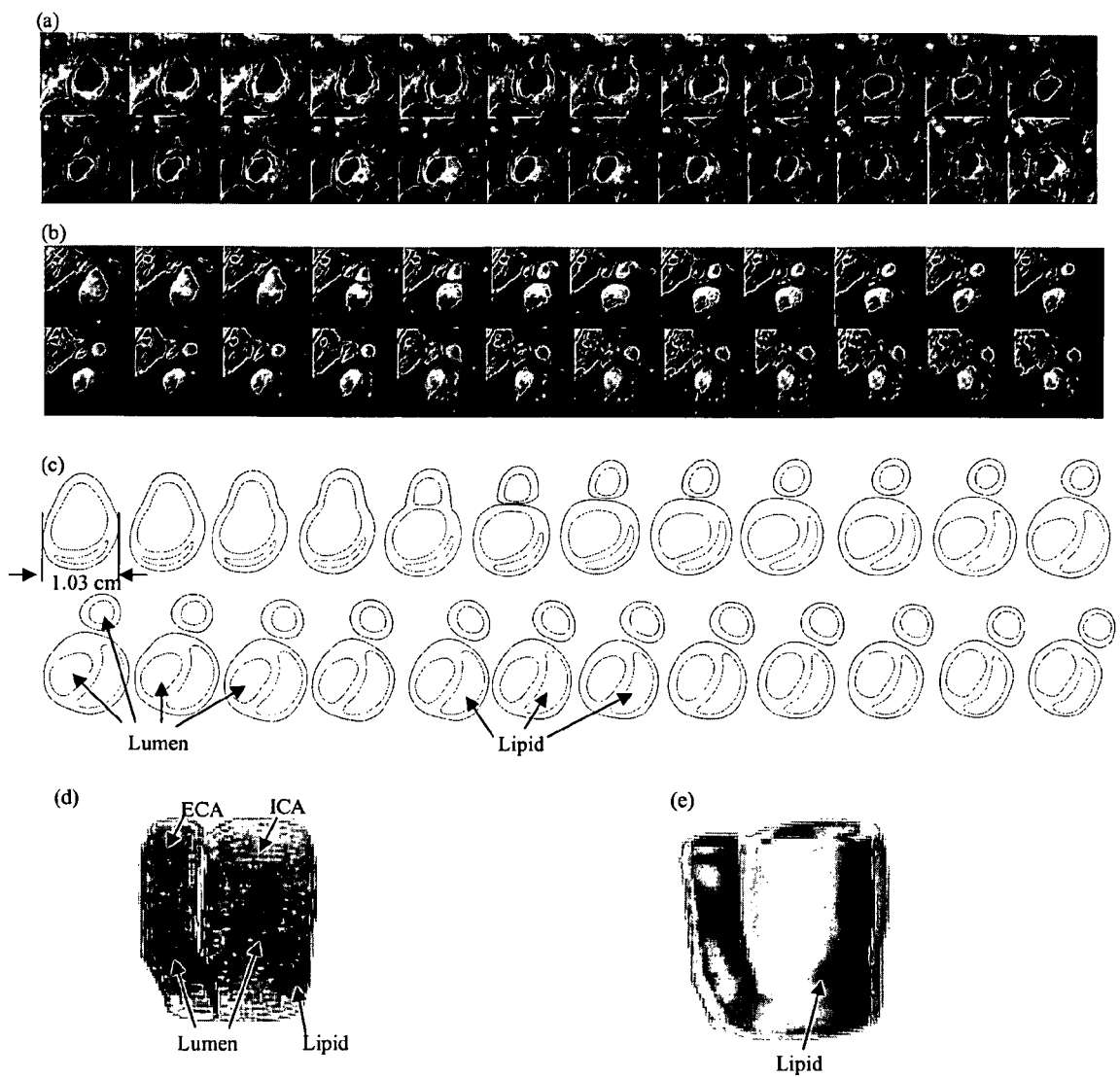
FIGS. 26(a)-26(b) are in vivo 3D MRI images of a human carotid: (a) 24 MRI (T1) slices (S0-S24) selected from a 24-slice set, slice spacing: 0.5 mm (each image shown here is cut from the whole-neck image; (b) Time-Of-Fly (TOF) images.
FIGS. 26(c)-26(e) are plaque and 3D reconstructions of the human carotid of FIGS. 26(a) and 26(b); (c) segmented contour plots using CASCADE showing plaque components; (d) re-constructed geometry with contour lines; (e) 3D geometry showing lipid core and lumen.

FIGS. 23(a)-23(c) show maximal principal stress and maximal principal strain plots on the same cut-surface. Flow pressure and velocity at three selected times on a cut-surface are shown in FIGS. 24(a)-24(c) and 25(a)-25(c). The cut-surface was slanted so that both inlet and outlet could be shown. Other quantities such as RV volume changes and strain energy function values could be calculated easily for further analysis based on the results obtained. The results indicated that stress/strain distributions were closely related to RV morphology, material properties and patient blood flow/pressure conditions.

Example 4

In vivo MRI-Based 3D FSI Models for Human Atherosclerotic Plaques and Quantitative Assessment for Plaque Progression In this example, patient-specific 3D multi-component FSI models of human atherosclerotic plaques based on in vivo MRI images of human carotid atherosclerotic plaques were demonstrated.

Patients were recruited using an established recruitment protocol approved by University of Washington Institutional Review Board with informed consent obtained. A carotid phased array coil was used for all MRI scans. Multi-contrast images of carotid atherosclerosis were generated to characterize plaque tissue composition, luminal and vessel wall morphology and inflammation. A computer package CASCADE (Computer-Aided System for Cardiovascular Disease Evaluation) developed by the Vascular Imaging Laboratory (VIL) at the University of Washington (UW) was used to perform image analysis and segmentation. CASCADE allowed for all contrast weightings to be simultaneously displayed, indexed relative to the carotid bifurcation, and analyzed serially along the length of the carotid artery. CASCADE automated analysis tools were able to accurately identify specific plaque features, including the lumen, wall boundary, necrotic core, calcifications, and other components. Upon completion of a review, an extensive report was generated and segmented contour lines for different plaque components for each slice are stored as digital files for 3D geometry reconstruction.

3D geometry reconstruction and mesh generation were done using ADINA as described in Example 1. FIGS. 26(a)-26(e) show 24 MRI slices (T1W and TOF) of a human carotid plaque sample (FIGS. 26(a) and 26(b)), the segmented component contour plots (FIG. 26(c)), and the re-constructed 3D geometry (FIGS. 26(d) and 26(e)). The diameter of the vessel was about 10 mm (outer diameter including vessel wall). Some smoothing (third-order spline) was applied to correct numerical and MRI artifacts, as well as overly sharp angles in the contour lines that affect the convergence of the model. The vessel was extended uniformly at both ends by 3 cm and 6 cm respectively so that it became long enough for our simulations. Geometries of other plaque samples were constructed using the same procedures.

Computational simulations were conducted with pressure conditions, cap thickness, stenosis severity and plaque components varied to observe the corresponding changes of flow and stress/strain behaviors, as conducted in Examples 1 and 2. Flow velocity, shear stress, pressure and plaque stress/strain distributions on different cut-surfaces were examined for critical patterns that may be related to plaque progression and rupture, as described in Example 2, to obtain an assessment of plaque progression and rupture.

While this invention has been particularly shown and described with references to preferred embodiments thereof, it will be understood by those skilled in the art that various changes in form and details may be made therein without departing from the scope of the invention encompassed by the appended claims.

For example, the present invention may be implemented in a variety of computer architectures. The computer of FIG. 3 is for purposes of illustration and not a limitation of the present invention.

The invention can take the form of an entirely hardware embodiment, an entirely software embodiment or an embodiment containing both hardware and software elements. In a preferred embodiment, the invention is implemented in software, which includes but is not limited to firmware, resident software, microcode, etc.

Furthermore, the invention can take the form of a computer program product accessible from a computer-usable or computer-readable medium providing program code for use by or in connection with a computer or any instruction execution system. For the purposes of this description, a computer-usable or computer readable medium can be any apparatus that can contain, store, communicate, propagate, or transport the program for use by or in connection with the instruction execution system, apparatus, or device.

What is claimed is:

1. A method for providing an assessment for disease status of a disease in which each step of the method is performed on a computer, comprising the steps of:
   a) constructing a computational, three-dimensional model of an organ representative of said disease status of a disease based on data for the organ, wherein the organ data includes image data of the organ, and the three-dimensional model includes a fluid-structure interaction and multiple components of the organ;
   b) computationally obtaining a certain mechanical distribution using the three-dimensional organ model; and
   c) computationally applying quantitative analysis of the mechanical distribution to provide a quantitative assessment for disease status of a disease, including providing a mechanical biological index that quantifies a degree of the disease status and identifies vulnerability of a plaque to rupture, vulnerability to rupture being based on histopathological plaque classifications.

2. The method of claim 1, wherein the organ data includes any combination of patient-specific data, morphology data, deformation data and fluid flow information data, of the organ.

3. The method of claim 1, wherein the disease is a cardiovascular disease.

4. The method of claim 1, wherein said multiple components include solid and liquid components within the organ.

5. The method of claim 1, wherein said fluid-structure interaction includes a blood-vessel interaction.

6. The method of claim 1, wherein said mechanical distribution includes a stress and strain distribution.

7. The method of claim 6, wherein said stress and strain distribution is modeled under an unsteady condition.

8. The method of claim 1, wherein the organ data includes any of: magnetic resonance imaging data of the organ and ultrasound technology data of the organ.

9. The method of claim 1, wherein said quantitative analysis further includes the steps of:
   identifying one or more critical sites where plaques are vulnerable to rupture;
   analyzing a certain mechanical distribution on the critical sites using the three-dimensional model;
   analyzing pathological data of plaques, and classifying vulnerability of the plaques used for pathological analysis in a numeric format, thereby providing a standard value for plaques vulnerability to rupture;
   scaling the plaques at the critical sites in a numeric format by comparing the plaques at the critical sites and the mechanical distribution on the critical sites with the standard value; and
   regressively correlating the numerical values of the plaques at the critical sites with the standard value, such that said numerical assessment for plaque rupture is provided.

10. The method of claim 9, wherein the analyzing a certain mechanical distribution includes quantifying at least one of: effect of pulsating pressure condition, effect of plaque cap thickness and effect of material property of a component of plaque, on the mechanical distribution.

11. The method of claim 9, wherein the mechanical distribution is a stress and strain distribution of the plaque.

12. The method of claim 9, further including the step of validating said numerical assessment for plaque rupture with clinical data.

13. A computer system, comprising:
   a) a data source containing data of an organ representative of disease status of a disease, the organ data including image data of the organ;
   b) a modeler coupled to receive data from the data source, the modeler generating a three-dimensional model of the organ based on the organ data, said model including a fluid-structure interaction and multiple components of the organ; and
   c) a routine for computationally obtaining a certain mechanical distribution using the three-dimensional organ model and for applying computational, quantitative analysis of the mechanical distribution, wherein the quantitative analysis of the mechanical distribution provides a quantitative assessment for said disease status of a disease, including providing mechanical biological index that quantifies a degree of the disease status and identifies vulnerability of a plaque to rupture, vulnerability to rupture being based on histopathological plaque classifications.

14. The computer system of claim 13, wherein the organ data includes at least one of patient-specific data, morphology data, fluid flow and deformation data, of the organ.

15. The computer system of claim 13, wherein the organ image data includes any of: magnetic resonance imaging data of the organ and ultrasound technology data of the organ.

16. The computer system of claim 13, wherein said multiple components include solid and liquid components within the organ.

17. The computer system of claim 13, wherein the routine solves the three-dimensional model by employing a nonlinear incremental iterative procedure to handle a fluid-structure interaction.

18. The computer system of claim 13, wherein said quantitative analysis of the mechanical distribution includes identifying correlation between said mechanical distribution and disease status of a disease, and quantifying the correlation.

19. The computer system of claim 18, wherein the assessment for disease status shows the quantified correlation between the mechanical distribution and disease status.

20. The computer system of claim 13, wherein the disease is a cardiovascular disease.

21. The computer system of claim 13, wherein said organ model is a three-dimensional model of an artery having a plaque.

22. The computer system of claim 13, wherein said model is a model of heart muscles.

23. The computer system of claim 22, wherein said modeler includes a field force introducing a force to govern heart muscle contraction and relaxation.

* * * * *